United States Patent [19]

Ohkuma et al.

[11] Patent Number: 5,358,729
[45] Date of Patent: Oct. 25, 1994

[54] INDIGESTIBLE DEXTRIN

[75] Inventors: Kazuhiro Ohkuma, Sanda; Isao Matsuda, Itami; Yoshiki Nogami, Kobe, all of Japan

[73] Assignee: Matsutani Chemical Industries Co., Ltd., Hyogo, Japan

[21] Appl. No.: 934,386

[22] Filed: Aug. 25, 1992

[30] Foreign Application Priority Data

Aug. 28, 1991 [JP] Japan .................................. 3-244587
Jul. 17, 1992 [JP] Japan .................................. 4-213627

[51] Int. Cl.$^5$ .................. A23L 1/308; A23L 1/09; A23L 1/31; A23L 1/325
[52] U.S. Cl. .................. 426/567; 127/28; 127/29; 127/30; 426/3; 426/48; 426/446; 426/450; 426/549; 426/550; 426/559; 426/561; 426/570; 426/589; 426/578; 426/579; 426/603; 426/613; 426/661; 536/103; 435/96; 435/99; 435/103
[58] Field of Search .......... 426/3, 48, 250, 446, 426/450, 549, 550, 559, 561, 589, 567, 570, 578, 661, 603, 613, 579; 514/58; 435/103, 96, 99; 127/28, 30, 29; 536/102–103

[56] References Cited

U.S. PATENT DOCUMENTS

| | | | |
|---|---|---|---|
| 3,137,592 | 6/1964 | Protzman et al. | 127/28 |
| 3,652,294 | 3/1972 | Marotta et al. | 426/250 |
| 4,230,503 | 10/1980 | Hughes | 127/28 |
| 5,131,953 | 7/1992 | Kasica et al. | 127/65 |

FOREIGN PATENT DOCUMENTS

| | | |
|---|---|---|
| 510977 | 7/1980 | Australia . |
| 0368451 | 5/1990 | European Pat. Off. . |
| 0443788 | 8/1991 | European Pat. Off. . |
| 0477089 | 3/1992 | European Pat. Off. . |
| 2268473 | 11/1975 | France . |

OTHER PUBLICATIONS

Derwent Abstract 90-004066/01 of J01287101 (Nov. 1989) Nippon Shokuhin Kak KK.
Chemical Abstracts, vol. 112, No. 18, Nov. 17, 1989, Columbus, Ohio, US; Abstract No. 160929u.
Database WPI, Week 7933, Derwent Publications Ltd., London, GB; AN 79-60543B.

*Primary Examiner*—Herbert J. Lilling
*Attorney, Agent, or Firm*—Sughrue, Mion, Zinn, Macpeak & Seas

[57] ABSTRACT

An indigestible dextrin characterized in that the dextrin contains:

(A) up to 50% of 1→4 glycosidic linkages, and
(B) at least 60% of an indigestible component,
(C) the content of indigestible component as actually determined varying within the range of ±5% from a value Y calculated from at least one of equations, i.e., Equations 1 to 62, given in the specification,
(D) the indigestible dextrin being prepared by adding hydrochloric acid to corn starch and heating the corn starch at 120° to 200° C. using an extruder, the value Y being a calculated content (%) of the indigestible component.

19 Claims, 9 Drawing Sheets

(PH 4.5)

INDIGESTIBLE DEXTRIN

BACKGROUND OF THE INVENTION

1. Field of the Invention

The present invention relates to indigestible dextrin prepared by heat-treating corn starch with addition of an acid.

2. Description of the Prior Art

Heat-treated starch (pyrodextrin) is prepared by heating a starch containing several percent water in the presence or absence of an acid. The glucose forming the starch consists primarily of 1→4 and 1→6 glycosidic linkages with very few 1→3 and 1→2 glycosidic linkages as is already known.

The proportion of these glycosidic linkages are disclosed only in J. D. Geerdes et al., J. Am. Chem. Soc., Vol. 79, 4209 (1957), G. M. Christensen et al, J. Am. Chem. Soc., Vol. 79, 4492 (1957) and the literature mentioned below. Commercial corn starch heat-treated with addition of hydrochloric acid comprises at least 57.3% of 1→4 glycosidic linkage fraction (2,3,6-Tri-O-Methyl-D-glucose), 2.6% of 1→6 glycosidic linkage fraction (2,3,4-Tri-O-Methyl-D-glucose), up to 1.2% of 1→3 glycosidic linkage fraction (2,4,6-Tri-O-Methyl-D-glucose), and 6.3% of a fraction having both 1→4 and 1→6 linkages (2,3-Di-O-Methyl-D-glucose).

R. L. Whistler and E. F. Paschall, Starch Chemistry & Technology, Vol. 1, p. 430 (1965) makes reference to analyzed values of linkage types constituting heat-treated amylopectin and heat-treated amylose obtained by separating corn starch into amylopectin and amylose fractions and individually heating the fractions with addition of an acid. The analyzed values obtained for the heat-treated fractions were prepared by gelatinizing corn starch, then separating the starch into the two fractions and heating each fractions. The crystalline structure of powder heat-treated thus differs from that of natural starch, so that the values can not be directly used for comparison. However, in view of the fact that the ratio between the two fractions of usual corn starch is about 8:2, the analyzed values, when calculated for corn starch correspond to 67% of 1→4 glycosidic linkage fraction (2,3,6-Tri-O-Methyl-D-glucose), 2.7% of 1→3 glycosidic linkage fraction (2,4,6-Tri-O-Methyl-D-glucose), and 7.8% of a fraction having both 1→4 and 1→6 linkages (2,3-Di-O-Methyl-D-glucose).

U.S. Pat. No. 2,274,789 discloses a prior-art process for preparing heat-treated starch and an apparatus therefor. This patent discloses a continuous treatment wherein hydrochloric acid is continuously added to a starch with a water content of about 45%, the starch dried in the form of a fluidized bed, heated at 105° to 260° C. and cooled to obtain a product of stable quality free of the hazard of explosion.

U.S. Pat. No. 2,332,345 discloses a process wherein starch is heated at 120° to 176° C. with stirring in a cylindrical container equipped with a steam jacket to obtain a product which has excellent properties as to adhesion, body smoothness of paste, stability and permanence of paste fluidity and shortened time of drying.

U.S. Pat. No. 2,565,404 discloses a process for preparing a starch sugar easily by adding hydrochloric acid to a powdery or wet starch, heating the starch to about 100° C. in an autoclave equipped with a stirrer while introducing a gas into the autoclave and heating the starch to about 130° C. with introduction of steam.

U.S. Pat. No. 2,698,818 discloses a process for preparing a product having a high quality over a wide range by drying starch in a vacuum within an autoclave with stirring and heating, and further heating the starch to 168° C. in a vacuum with introduction of hydrogen chloride gas.

U.S. Pat. No. 2,818,358 discloses a process which comprises adding hydrochloric acid to starch, then feeding the starch into a heated spiral coil, and heating the starch to 115° to 160° C. within a short period of time while moving the starch through the spiral coil by vibrating the coil, whereby a uniform product is continuously prepared with a high thermal efficiency.

U.S. Pat. No. 2,845,368 discloses a process wherein vaporized hydrochloric acid is added to starch while the starch is being fluidized by introduction of a gas so as to react the starch under widely varying conditions by heating the starch in the fluidized state within a short period of time.

U.S. Pat. No. 3,200,012 discloses a process comprising adding hydrochloric acid to starch in the form of fine particulate and feeding the starch into a rotative drum internally provided with a heating tube to heat the starch and continuously obtain a product having a diminished reducing sugar content and good solution stability.

Furthermore, Tomasik, P. and Wiejak, S., Advance in Carbohydrate Chemistry, Vol. 47, 279–343 (1990) generally describes the latest information as to heat-treated starches.

When analyzed, the products of the foregoing processes were found to contain up to 30% of indigestible fraction. When starch was heated under altered conditions to obtain a higher indigestible content, it was possible to increase the content to about 60%, whereas the product then contained an increased amount of colored substance, had a stimulative odor, therefore required purification, and was not practically useful because of extreme difficulties encountered in refining the product. Accordingly, the conventional processes fail to afford a product which contains about 60 to 90% of indigestible fraction as contemplated by the present invention.

As to the decomposition of carbohydrates with use of an extruder, U.S. Pat. No. 4,316,747 discloses a process wherein a cellulose slurry containing an acid added thereto is heated in a twin-screw extruder under an increased pressure to prepare glucose.

With improvements in living standards in Japan in recent years, eating habits have changed and become similar to those of American and European people. This trend has resulted in a lengthened average life span and a rapidly aging society with marked increases in degenerative diseases. Manifestly, people have become health-oriented. Attention has, therefore, been directed to dietary fibers and oligosaccharides enhance the function of foods and livestock feeds in that these materials are known to alleviate constipation and other desired biological regulatory functions.

Indigestible substances, such as dietary fibers and oligosaccharides, exhibit various modes of behavior in the digestive tracts producing physiological effects on the living body. First in the upper digestive tract, water-soluble dietary fibers slow the transport of food and delay the absorption of nutrients. Delayed absorption of sugar, for example, suppresses the rise in blood sugar value, consequently lowering insulin requirements. Further, excretion of bile acid is promoted, diminishing the sterol group in the body thereby lowering the cholesterol level of the serum. Other physiological effects through the endocrine system of the body are also reported.

Another feature of these indigestible substances is they are not digested or absorbed by the digestive tract, including the small intestine and reach the large intestine. On reaching the large intestine, oligosaccharides and dietary fibers are partly acted on by enterobacteria yielding short-chain fatty acids, intestinal gases, vitamins, etc. Acidification of the intestinal environment by the short-chain fatty acids condition the intestine. It has also been reported that when absorbed, these short-chain fatty acids are metabolized to provide energy and, simultaneously, inhibit the synthesis of cholesterol. Therefore, ingestible substances are necessary in obtaining these desired physiological effects.

A "dietary fiber hypothesis" suggested by Trowell and Burkitt epidemilogically revealed that there is a negative correlation between the intake of dietary fibers and the onset of non-infectious diseases such as cholelithiasis, ischemic heart diseases, cancer of the large intestine, etc. Thus, insufficient ingestion of dietary fibers is thought to be a cause of degenerative diseases which are said to be diseases of the Western type. The dietary fibers are defined as the "whole group of indigestible components of foods which are not digestible by human digestive enzymes" and are classified into insoluble dietary fibers and water-soluble dietary fibers according to the solubility in water. Of these, water-soluble dietary fibers have attracted attention as materials for functional foods and livestock feeds because of their great physiological function.

For example, it is said that high viscosities inhibit diffusion of sugar, resulting in delayed absorption of sugar and reduction in the rise of blood sugar value, consequently lowering insulin necessity. Further it is said that promoted excretion of bile acid into feces by water-soluble dietary fibers diminishes cholesterol in the serum, and that after reaching the large intestine, the dietary fibers are acted on by enterobacteria to produce lactic acid and acetic acid with these organic acids lowering the pH within the large intestine and preventing cancer of the large intestine.

Examples of such water-soluble dietary fibers include guar gum, glucomannan, pectin and like natural gums which have high viscosity which are difficult to ingest singly in a large amount. Further the addition of these fibers to processed foods encounters problems in preparing the food and presents difficulties with respect to texture. It has therefore long been desired to provide dietary fibers of low viscosity which have the same physiological functions as the above fibers, are easy to ingest and are user-friendly in preparing processed foods.

In recent years in Japan, processed foods, precooked foods, fast foods and the like have found wider use with the maturity of economical environments and the resulting improvements in food processing techniques and distribution techniques. With this trend, diversified information as to the ingestion of foods has become available, and eating habits to fulfill the nutrient requirements are changing to health-oriented dietary habits contemplated for the prevention of nutrition disorders and degenerative diseases due to eating habits. Especially, people of middle or advanced age and young women have much need for low caloric foods, so that low caloric sweeteners and bulking agents for strong sweetening agents have been developed. Among these, low caloric sweeteners include various indigestible oligosaccharides and sugar alcohols, which nevertheless have many problems with respect to the quality, degree of sweetness, oligosaccharide content and likelihood of causing laxation.

The bulking agent available for use with strong sweetening agents such as aspartame is polydextrose only, whereas polydextrose is ingestible in a limited amount, tastes bitter in an acid condition, is hygroscopic and therefore has problems. In view of the situation described, it has been desired to provide a low caloric bulking agent which fulfills the requirements for use as a food and which is usable for sweeteners and the like with safety.

On the other hand, starch is used in large quantities in various processed foods as a food material. Useful food materials of these types include starch and starch products such as pregelatinized starch, pyrodextrin, and its derivatives, glucose, corn syrup solids and maltodextrin. However, a majority of these starch products are not higher than 5% in the content of indigestible component and at least 3.9 kcal/g in caloric value, so that among starches and like materials, only pyrodextrin appears useful as a dietary fiber and low caloric material. Heat-treated starch (pyrodextrin) will hereinafter be referred to merely as "dextrin".

We conducted continued research on processes for preparing dextrin, starch hydrolysis processes and processes for preparing indigestible dextrin from dextrin. Based on the results obtained, we have already filed a patent application for an invention entitled "Process for Preparing Dextrin Food Fiber". Our research, subsequently carried out on the physiological activities of the dextrin, revealed that the dextrin had an improvement in intestine conditions, amelioration in hypercholesterolemia, a lowering insulin requirements, a hypotensive effect and a lower caloric value, i.e. effects similar to those of dietary fibers. Based on the finding, we have filed a patent application for the dextrin as a food composition.

We have also investigated the correlation between the structure of dextrin and the content of indigestible fraction thereof and found that the content of indigestible component of dextrin is in inverse proportion to the amount of 1→4 glycosidic linkages of dextrin among other glycosidic linkages thereof. We have further conducted detailed research.

The research thus conducted on various dextrins indicates that the indigestible component is closely related with the quantities of 1→4, 1→6 and like glycosidic linkages, and statistical numerical analyses afforded equations representing a high degree of correlation there-between.

With the prior-art reaction conducted at atmospheric pressure, the velocity of reaction is a function of the time and temperature, i.e., reaction conditions, whereas the heat treatment of starch under increased pressure is entirely different from the conventional reaction in that the correlation between 1→4 and 1→6 linkages and the indigestible fraction can be expressed by a special function, i.e., equation. This is a novel finding we obtained. Nevertheless, the dextrins obtained by conventional techniques are as low as 5 to 30% in the content of indigestible component, contain a colored substance or release a stimulative odor even if obtained by a high-temperature long-time reaction, and are in no way actually usable.

SUMMARY OF THE INVENTION

Accordingly, the main object of the present invention is to provide a novel indigestible dextrin containing up to 50% of 1→4 glycosidic linkages and at least 60% of indigestible component and diminished in colored substance or stimulative odor.

This object can be accomplished basically by providing a dextrin which contains an indigestible component in an increased amount of at least 60%.

DETAILED DESCRIPTION OF THE INVENTION

The analytical data given herein is expressed as data as to anhydrous substances, while values as to water-containing substances are given in Examples of food and feed, unless otherwise specified. And dietary fiber and caloric values of foods and feeds component other than indigestible dextrins are calculated values according to "Standard Tables of Food Composition in Japan" 4th revised Ed., (1982), Resources Council, Science and Technology Agency, Japan. Also the glucose residue composed solely of 1→4 bonds is expressed as "glucose residue having 1→4 bonds" further, 1→6 and 1→3 bonds are expressed as above.

The starch to be used as a material for indigestible dextrin according to the invention is corn starch, and the treatment to be conducted essentially requires addition of an acid to the starch as a catalyst. While various acids are usable, hydrochloric acid is especially desirable to use since the product is used for foods. The indigestible dextrin obtained must contain at least 60% of an indigestible component, as required for the dextrin to exhibit biological regulatory effects.

Incidentally, dextrins include white dextrin which has heretofore been generally used for foods and medicines. This dextrin contains about 5% of indigestible component and therefore is not usable for applications wherein biological regulatory effects are required. Further conventional yellow dextrin, when containing at least 30% of indigestible component, has a stimulative taste and is accordingly unusable.

Examples of apparatus desirable for use in the process of the invention for conducting heat-treatments under a high pressure are extruders for use in preparing snack foods and the like.

Twin-screw extruders are most desirable to use.

Figure 8:
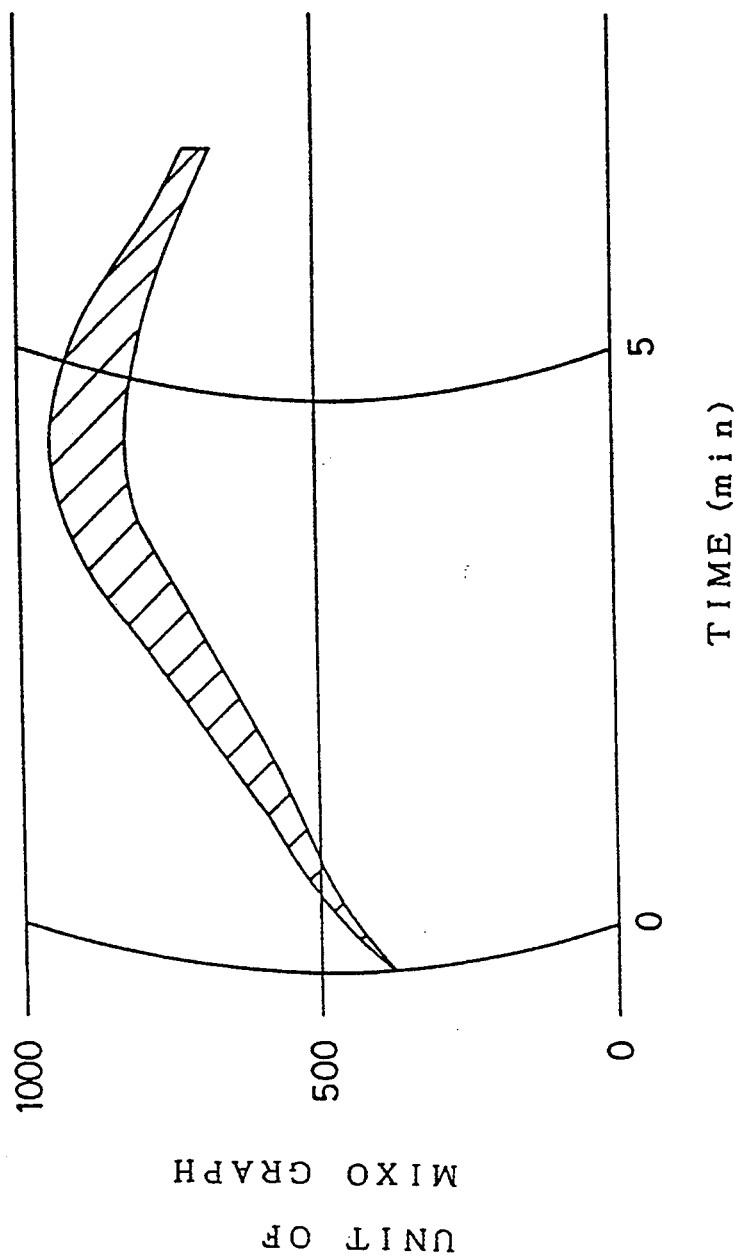
FIG. 8 is a mixograph of a sugar group.

Extruders, which are used for extruding materials under an increased pressure, are divided generally into those having a single rotative screw inserted in a cylinder, and those having two rotative screws in the same direction or reverse direction and inserted in cylinders arranged in the shape of the FIG. 8 in cross section. Although extruders of either type are usable in this invention, twin-screw extruders are especially preferred. The screw or screws are generally demountable, and can be of various types with respect to the pitch, including reverse pitch type. Screws of varying pitches can be used in a suitable combination. With some extruders, suitable screws are selectively usable in accordance with the properties of the material to be treated. Usually, the material is fed to the extruder at one end of the screw in rotation with the cylinder heated, and is heated under an increased pressure while also utilizing the heat of friction between the screw and the material.

Extruders of either type are 30 to 340 mm in the diameter of the screw and about 10:1 to about 45:1 in the ratio of the length of the screw to the diameter thereof. The extruder is heated with steam or by electric or induction heating. The actual operation of the extruder requires a material container, material feeder, product cooling device, product transport device, product container, etc.

The extruder (either of the single-screw or twin-screw type) is operated heated at 120° to 200° C. Further to use the extruder as a reactor, it is essentially required that the material and the product be smoothly movable through the extruder. The rotating speed of the screw is closely related also with the properties of the material, heating temperature, reaction time and the amount of acid added, and must be optimally determined based on the content of indigestible component of the product. Usually, it is 120 to 400 r.p.m.

Hydrochloric acid is used in the form of an aqueous solution having a concentration of about 1%, and is added to the material starch in an amount of 3 to 10 wt % based on the starch. Since the acid solution is added to the starch before the heat treatment, the solution and the starch are mixed together uniformly by being stirred in a mixer and aged therein. The mixture is then preheated at about 100° to about 120° C. to a water content of about 8% which is slightly higher than is the case with the prior-art heating process using atmospheric pressure. The material is thereafter continuously fed to the extruder for heat treatment, and the product discharged from the outlet of the extruder is rapidly cooled to complete the heat treatment.

The heat treatment by the extruder is most distinctly characterized in that starch is continuously reacted in a molten state. Whereas the starch as heat-treated by the conventional method remains in the form of a powder despite the treatment, the starch as heat-treated in a molten state is in an amorphous form.

Higher reaction temperatures result in increases in the content of indigestible component, but very high temperatures are not desirable since the product contains an increased amount of colored substance when the temperature exceeds about 170° C. Stated specifically, the reaction temperature is 120° to 200° C., preferably 130° to 180° C., more preferably 140° to 180° C.

For a better understanding of the features of the present invention, experimental data will be described below in detail.

EXPERIMENTAL EXAMPLES

1. Method of Determining the Content of Indigestible Component

The content was measured by a modified method according to "The method for determining the indigestible part using HPLC" (Journal of Japanese Society of Starch Science, Vol. 37, No. 2, p. 107, 1990) as will be described below.

One gram of a sample was accurately weighed out, and 50 ml of 0.05M phosphate buffer (pH 6.0) was added to the sample, followed by addition of 0.1 ml of Termamyl (alpha-amylase, product of NOVO Industry Co., Ltd.) and reacted at 95° C. for 30 minutes. The reaction mixture was cooled and adjusted to a pH of 4.5. A 0.1 ml quantity of amylo-glycosidase (product of Sigma) was added to and reacted with the mixture at 60° C. for 30 minutes, followed by heating to 90° C. to complete the reaction. After completion of the reaction, the reaction solution is filled up to 100 ml with water and subjected to the determination of the content of glucose present therein by the pyranose-oxidase method and thus the content of the indigestible components (%) is calculated from the resulting glucose content (B) and that of the sample (A), separately determined in the same manner, prior to the reaction according to the following relation:

The content of indigestible components (%) by weight)=$[1-A-(B-A) \times 0.9] \times 100$ wherein A is glucose content (g) prior to the reaction and B is glucose content (g) after the reactions.

2. Method of Quantitatively Determining Glycosidic Linkages

A sample was methylated by a modified method of Hakomori's methylation method (S. Hakomori, J. Biochem., 55, 205 (1964)) described below, followed by hydrolysis and thereafter by gas chromatography to quantitatively determine the glycosidic linkages composing the sample.

(1) Methylation

A dehydrated sample (100 to 200 μg) is placed into a test tube (15 mm diam. × 100 mm) with a screw cap and dissolved by addition of 0.3 ml of DMSO. To the solution is added 20 mg of NaH, immediately followed by addition of 0.1 ml of methyl iodide. The mixture is stirred by a touch mixer for 6 minutes and then cooled in ice water, and 2 ml of water is added to the mixture. The mixture is fully shaken with addition of 2 ml of chloroform. The upper layer (aqueous layer) is collected with a pipette and discarded. The remaining layer is similarly washed with addition of 2 ml of water. This procedure is repeated 6 times. Cotton is placed on the bottom of a Pasteur pipette, anhydrous sodium sulfate is placed into the pipette to form a 4- to 5-cm-thick layer, and the solution is passed through the layer for dehydration and then washed with chloroform. Subsequently, the solution is concentrated to dryness in a rotary evaporator.

(2) Hydrolysis

With addition of 0.5 ml of trifluoroacetic acid, the methylated product is hydrolyzed at 100° C. for 4 hours, and the hydrolyzate is concentrated to dryness at 60° C. in a rotary evaporator.

(3) Reduction

The hydrolyzate is dissolved in 0.5 ml of water, and the solution is allowed to stand at room temperature for 2 hours with addition of 10 mg of sodium borohydride. Several drops of acetic acid are added to the mixture until the mixture ceases foaming to terminate the reaction. The mixture is then dried at room temperature and further dried at room temperature with addition of 1 ml of methanol to remove the boric acid formed. This procedure is repeated 6 times.

(4) Acetylation

With addition of 0.5 ml of acetic anhydride, the reduced product is heated at 100° C. for 4 hours and thereby acetylated. With addition of 1 ml of toluene, the product is concentrated to dryness in a rotary evaporator.

(5) Desalting

The acetylated product is dissolved in 1 ml of chloroform, the solution is shaken with addition of 1 ml of water, and the aqueous layer is discarded. After repeating this procedure 5 times, the chloroform is evaporated off from the resulting layer by a rotary evaporator.

(6) Dissolving

The desalted product is dissolved in 0.5 ml of chloroform and subjected to gas chromatography.

(7) Conditions for gas chromatography

Column: DB-1 fused silica capillary column 60 m × 0.255 m × I.D., 0.1 μm film

Column temperature: 50° C. for 1 minute, elevation of temperature at a rate of 10° C./min to a constant temperature of 280° C.

Temp. of sample vaporizing chamber: 300° C.

Detection temp.: 300° C.

Flow rate: 2.5 ml/min, helium

Detecting unit: flame ionization detector

3. Method of Quantitatively Determining Dietary Fiber Content

Dietary fibers are quantitatively determined by the following Prosky method (No. 985.29, Total Dietary Fiber in Foods, "Official Methods of Analysis", AOAC, 15th Ed., 1990, P.1105~1106, No. 985.29, Total Dietary Fiber in Foods).

4. Method of Measuring Caloric Value-1

Measurements were carried out according to the following method titled "Measurement of Physiological combustion Heat of Food for Specified Health Use Containing Water-Soluble Low Caloric Sugars" which is notified by the Ministry of Health and Welfare of Japan.

4-1. Reagent and Others

(1) Somogy copper Reagent 90 g of potassium sodium tartrate and 225 g of Na PO 12$H_2O$ were dissolved into water, then 30 g of Cu-$SO_4$-5$H_2O$ and 3.5 g of K10 were sequentially added, then filled up with distilled water to 1,000 ml.

(2) Lowry Reagent

Solution A: Prepared by Mixing 1% $CuSO_4 \cdot 5H_2O$ and 2.2% Potassium sodium tartrate by the ratio of 1 to 1.

Solution B: prepared by mixing phenol and distilled water by the ratio of 1 to 0.8.

(3) Sugar-Alcohol Measuring Kit

F-kit: F-kit for D-sorbitol/xylitol (produced by Boeringer Manheim Yamanouchi)

(4) Diastase Solution

2% diastase (Japanese Pharmacopoeia) solution.

(5) Hydroxylamine Pyridine Solution

Prepared by dissolving 100 ml of hydroxylamine into 10 ml of pyridine.

(6) Conditions of gas chromatography

F1D gas chromatograph; 5% SE30 chromosolb W; glass column or stainless steel column of 3 to 4 mm of internal diameter and 2 m in length; column temperature 185° C.; and carrier gas of 80 ml/min.

4-2. Measurement of Total Water-Soluble Reducing Sugars (1) Preparation of a Test Solution If a sample includes oligosaccharides alone, they are extracted using water or 80% ethanol, and if including polysaccharides, then oligosaccharides should be completely extracted using 80% ethanol. The extracted solution was then concentrated under reduced pressure (at lower than 60° C.), and residue was completely dissolved into a small amount of 50 mM maleic acid-Na buffer to finally obtain about 500 mg % of glucose.

(2) Procedure 1N-hydrochloric acid was added to the test solution by the ratio of 2:1 and the mixture was heated at 100° C. for 20 hours in boiling water bath. After cooling, the solution was neutralized with 1N-sodium hydroxide (bromothymol blue test paper). Then the content of reducing sugars of the obtained solution was measured by Somogy's method, and the content of 5,6 carbonic sugar alcohol was measured by gas chromatography or F-kit. The sum of the sugars thus obtained represents the total amount of water-soluble sugars (A).

(3) Somogy Method 2.5 ml of Somogy solution was added to 7.5 ml of the test solution (of which reducing sugar were 1 to 10 mg) and the mixture was heated at 100° C. for 10 minutes. After cooling, 2 m of 5% KI and 3 ml of 1,2N-sulfuric acid were added to the solution and mixed well. Then this mixture was titrated with $1/40N-Na_2SO_3 \cdot 5H_2O$. Glucose was employed as a standard sugar. The amount of sugars was obtained by the titration value.

(4) Measurement of Sugar-Alcohol

The amounts of sorbitol and xylitol were determined with the use of F-kit by appropriately diluting the test solution which had been hydrolyzed for the purpose of the mentioned determination of total amount of water-soluble sugars.

In case of containing pentose and hexose alcohol other than sorbitol and xylitol, the determination was effected by gas chromatography. That is, the test solution which had been hydrolyzed for the determination of the total amount of water-soluble sugars, was concentrated under the reduced pressure at a temperature lower than 60° C., and, after adding ethanol so as to obtain a final concentration exceeding 80%, the solution was heated and extracted in the boiling water bath for 30 minutes. The extract was concentrated in vacuo at a temperature of lower than 60° C. 80% ethanol was added to this concentrated extract to obtain a specified amount thereof. Picking up 5 ml of the solution thus obtained, the solvent was completely removed therefrom under reduced pressure. The residue was dissolved into 1 ml pyridine, then 1 ml of hydroxylamine pyridine was further added, and, after leaving this solution for 5 minutes as it was, the solvent was removed under reduced pressure. 1 ml of benzene was added to the residue, and after removing completely $H_2O$ under reduced pressure, the residue were dissolved by adding 2 ml of pyridine. After the dissolution, 0.2 ml of hexamethyl disilane and 0.1 ml of trimethylsilane were added to the solution. After shaking for well mixing, the solution was left for 15 minutes at room temperature, and a specified amount of this solution was obtained by pyridine extraction and was then determined by absolute calibration curve method using gas chromatography.

4-3. Determination of Insoluble Starch (1) With respect to a sample containing starch, using a sample corresponding to 2.5 to 3.5 mg of dry material, the residue extracted with 80% ethanol obtained in the same manner as the mentioned extraction method of total water-soluble sugars, was dispersed into 200 ml water; the solution was then soaked into boiling water bath and heated for 15 minutes while being continuously stirred. Then, the solution was cooled down to 55° C. and, after adding 10 ml of diastase solution, left for one hour at 55° C. Subsequently, after boiling for several minutes, the solution was again cooled down to 55° C. then, adding 10 ml of diastase solution, was stirred well and left for one hour. At this time, when the residue in the reaction solution showed a positive reaction in the iodine starch reaction, diastase solution was further added, then digestion took plase. A distilled water was added to the diastase treated solution of which iodine starch reaction was negative, thereby obtaining 250 ml of mixed solution with distilled water, and then filtered through a filter paper. Hydrochloric acid was added to the filtered solution to be a 2.5% solution, and the mixture was heated in the boiling water bath for 2.5 hour. After cooling, the solution was neutralized with 10% sodium hydroxide, then the filtered solution was adequately diluted, and the content of glucose was determined by Somogy's method. The amount of glucose thus obtained was multiplied by 0.9 to obtain a starch amount (A').

4-4. Determination of Sugars Digested and Absorbed in the Small Intestine (1) Determination of Sugars Digested by Enzyme 1) Preparation of a solution of a commercially available rat small intestinal acetone powder 0.9% NaCl was added to a rat small intestinal acetone powder produced by Sigma to obtain a suspension (100 mg/ml). After conducting the ultrasonic treatment (60 sec, 3 times), the solution was centrifuged (3000 r.p.m., 30 min) and a supernatant thereof was recovered in the form of an enzyme solution. The protein amount of this enzyme solution was determined by Lowry's method. The solution was then subjected to an adjustment so that the enzyme activity thereof was about 0.1 mg/mg protein/hour as activity of sucrose hydrolysis.

2) Digestion Test Using a Rat Small Intestinal Acetone Powder

An extract with 80% ethanol prepared for the determination of the mentioned total amount of water-soluble sugars, or extract of water was concentrated, then diluted by 50 mM maleic acid-Na buffer (pH 6.0) so that the concentration of sugars be 1 to 4%, thus a sample being obtained. 1.0 ml of this solution and 1.0 ml of the enzyme solution were mixed and incubated for one hour at 37° C. After the incubation, the solution was heated for deactivation in the boiling water bath for 10 minutes. And after the centrifugation (3000 r.p.m., 30 min), with respect to the supernatant, the amount of the reducing sugars was determined by Somogy's method while the amount of sugar alcohol measured by F-kit or gas chromatography, the sum of these two measured amounts representing the amount of enzymatic digestive absorption sugars. At this time, the reducing sugars and sugar alcohol which existed as monosaccharide in the sample from the beginning were also measured. The decomposition percentage was obtained by dividing the amount of digestive absorption sugars by the total amount of water-soluble sugars and multiplied by 100. As a control experiment, the same process as the foregoing was conducted with respect to sucrose or maltose having the same amount of water-soluble sugars. In this control experiment, the decomposition percentage had to be more than 20% when the experiment was conducted on sucrose. Ratio of the mentioned decomposition percentage on sucrose or maltose to a decomposition percentage obtained from the tested sugars was to be as a small intestine digestive absorption ratio. This small intestine digestive absorption ratio was then multiplied by the total amount of water-soluble sugars to obtain a total amount of digestive absorption reducing sugars (B), and also multiplied by the total amount of sugar alcohol to obtain a total amount of digestive absorption sugar alcohols (C).

For the control experiment selecting whether sucrose or maltose is to be employed is performed by the following method. That is, a digestion test was carried out employing maltose as a substance in half amount of the tested sugars under the same conditions as the mentioned digestion test by a rat small intestinal acetone powder. In case glucose created by the digestion was not exceeding 10 times as much as the sum of sugars and sugar alcohol created in the digestion test of the tested sugars, maltose was employed as a control sugar. When exceeding 10 times, sucrose was employed.

3) Determination of Protein 0.3 ml of 1N-sodium hydroxide was added to 0.1 ml of sample (containing 20 to 100 mg of protein), and the mixture was left for 15 minutes at room temperature. 3.0 ml of the mentioned solution A was further added and the mixture was left for 10 minutes at room temperature. Then, 0.30 ml of the mentioned solution B was added, and after 30 minutes, the light absorbancy at a wave-length of 750 nm was measured. Cattle serumalbumin was employed as standard protein.

4-5. Calculation of Caloric Value-2

The physiological combustion heat value can be considered as the sum of the effective energies generated by the digestive absorption and the enzymatic absorption. Accordingly, the caloric value-2 can be calculated as follows:

The physiological combustion heat value (kcal/g)=(-Starch A')×4+(Total amount of digestive absorption reducing sugars (B))×4+(Total amount of digestive absorption sugar alcohol (C))×2.8+(Total water-soluble sugars (A))-(Total amount of digestive absorption reducing sugars (B)+Total amount of digestive absorption sugar alcohols (C))×0.5$^{(1)}$×1.9$^{(1)}$: Ratio of Fermentable sugar of indigestible dextrin in the large intestines.

5. Method of Measuring Caloric Value-2

The effective caloric value of a sample is calculated as the sum of the caloric value resulting from digestion and absorption by the digestive system up to the upper digestive tract, and the caloric value resulting from intestinal fermentation after arrival of the sample at the large intestine Test 1: Measurement of caloric value resulting from digestion and absorption by the upper digestive tract up to the small intestine The sample is dissolved in 45 mM (bis)Tris buffer (pH 6.0) containing 0.9 mM calcium chloride to obtain a 4.55% solution, to which 160 U/g of human saliva alpha-amylase (SIGMA Type IX-A) is added, followed by a reaction at 37° C. for 30 minutes. After deactivating the enzyme, the reaction mixture is desalted with an ion exchange resin and adjusted to a concentration of 1.1%. The aqueous solution (4 ml) is then added to 2 ml of 50 mM hydrochloric acid-potassium chloride buffer (pH 2.0), and the mixture is maintained at 37° C. for 100 minutes, followed by desalting with an ion exchange resin. To the desalted solution is added 45 mM (bis)Tris buffer (pH 6.0) containing 0.9 mM calcium chloride to adjust the solution to a concentration of 0.45%. To the solution is added 400 U/g of swine pancreatic amylase (product of Boehringer Mannheim Yamanouchi Co., Ltd.), followed by a reaction at 37° C. for 6 hours. The enzyme is then deactivated, and the reaction mixture is thereafter desalted with an ion exchange resin, concentrated and lyophilized.

The powdery sample thus obtained is dissolved in 45 mM sodium maleate buffer (pH 6.6) to prepare a 0.45% solution, with which 86 U/g of rat small intestine mucous membrane enzyme (product of SIGMA) is reacted at 37° C. for 3 hours. The amount of glucose produced is measured by the pyranose oxidase method. The caloric value to be produced by digestion and absorption is calculated from the following equation.

$$\text{Caloric value} = \frac{\text{Amount of glucose produced (\%)} \times 4\text{kcal/g}}{100}$$

Test 2: Determination of caloric value resulting from intestinal fermentation

The caloric value of the fraction reaching the large intestine was determined by the growth curve method using rats as described below.

TABLE 1

| Component | Proportion (%) |
|---|---|
| Corn starch | 42.7 |

TABLE 1-continued

| Component | Proportion (%) |
|---|---|
| Casein | 40.0 |
| Fiber | 2.0 |
| Mineral mixture | 10.0 |
| Vitamin mixture | 0.8 |
| DL-methionine | 0.3 |
| Choline bitartrate | 0.2 |
| Vegetable oil | 5.0 |

Rats were preliminarily raised for 5 days to adapt them to the laboratory environment and to the basal diet shown in Table 1, then checked for body weight and health and divided into groups (10 rats in each group). The average initial body weight of all the test groups was 79.6 to 80.8 g. The body weight variations of the groups were in the range of 9 to 16 g. The caloric value of all the test components and basal diet was measured by a bomb calorimeter.

TABLE 2

| No. | Basic diet (g) | Glucose (g) | Sample (g) | Total amount (g) | Caloric value (Kcal) |
|---|---|---|---|---|---|
| 1 | 5.4 | — | — | 5.4 | 22.7 |
| 2 | 5.4 | 0.5 | — | 5.9 | 24.7 |
| 3 | 5.4 | 1.0 | — | 6.4 | 26.7 |
| 4 | 5.4 | 2.0 | — | 7.4 | 30.7 |
| 5 | 5.4 | 4.0 | — | 9.4 | 38.7 |
| 6 | 5.4 | — | 0.5 | 5.9 | 24.7 |
| 7 | 5.4 | — | 1.0 | 6.4 | 26.7 |
| 8 | 5.4 | — | 2.0 | 7.4 | 30.7 |
| 9 | 5.4 | — | 4.0 | 9.4 | 38.7 |

After grouping, the rats were placed into individual steel cages and fed according to the experimental schedule listed in Table 2. The basal diet was given to all the rats in an amount of 5.4 g/rat/kg (22.7 kcal/rat/day). For the test groups, glucose or the above sample was added in an amount of 0.5, 1.0, 2.0 or 4.0 g to the basal diet. The amount of glucose or sample added was about 2, 4, 8 or 16 kcal/rat/day in terms of caloric value. The amount of ingestion was measured daily, and the gain in the body weight was measured on the 0th, 5th, 10th and 15th days. The rats were checked generally every day by observation. Table 3 shows the results.

TABLE 3

| No. | Body weight Initial g | Body weight Final g | Body weight Gain g/14 day | Consumed calories KCal/day | Calories needed for 1 g gain |
|---|---|---|---|---|---|
| 1 | 80.8 | 67.3 | −13.5 | 22.7 | — |
| 2 | 80.5 | 72.9 | −7.6 | 24.8 | — |
| 3 | 80.7 | 79.0 | −1.7 | 26.2 | — |
| 4 | 80.2 | 90.1 | 9.9 | 30.3 | 0.023 |
| 5 | 80.3 | 106.4 | 26.1 | 36.7 | 0.051 |
| 6 | 80.2 | 72.0 | −8.2 | 24.8 | — |
| 7 | 79.6 | 75.1 | −4.5 | 26.2 | — |
| 8 | 80.4 | 86.1 | 5.7 | 31.1 | 0.013 |
| 9 | 79.9 | 84.7 | 4.8 | 39.8 | 0.009 |

With reference to Table 3, the caloric value determined by the animat experiment is:

$$(0.013 \div 0.023 \times 3.8 + 0.009 \div 0.051 \times 3.8) \div 2 = 1.41 \text{ kcal/g}$$

From Test 1, the caloric value resulting from the digestion and absorption of the sample by the upper digestive tract is:

$$\frac{9.8 \times 4\text{kcal/g}}{100} = 0.39 \text{kcal/g}$$

Accordingly, the caloric value resulting from intestinal fermentation is:

$$1.41 - 0.39 = 1.02 \text{ kcal/g}$$

From this data, the caloric value produced by the intestinal fermentation of the dextrin is:

1.02 ÷ 0.912 (proportion reaching the large intestine) = 1.1 kcal/g = about 1 kcal/g Thus, according to the methods of Test 1 and Test 2, the caloric value was calculated from the following equation.

$$\text{Caloric value} - 2(\text{kcal/g}) = \frac{\text{Glucose produced (\%)} \times 4}{100} + \frac{(100 - \text{glucose produced (\%)}) \times 1}{100} = 1 + \frac{3 \times \text{glucose produced (\%)}}{100}$$

Experimental Example 1

Preparation of Dextrin by Extruder, Structure of Thereof and Analysis of Indigestible Component Using pressurized air, 22.5 liters of a 1% solution of hydrochloric acid was sprayed onto 300 kg of commercial corn starch placed in a ribbon mixer while rotating the mixer, and the mixture was then passed through a disintegrator to obtain a uniform mixture, which was further treated in the ribbon mixer for 1 hour and predried to a water content of about 8% by a flash dryer. A 270 kg portion of the mixture was continuously charged into a twin-screw extruder (Model TES 32FSS-20AW-V for foods, manufactured by Japan Steel Works, Ltd. and having screws rotative in the same or different directions on change-over, 32 mm in diameter and 20/1 in length/diameter, drive motor 7.5 KW in output and rotatable at 400 r.p.m. max., aluminum cast heater, water cooling system with vent hole) and heat-treated at a temperature of 130° C., 140° C., 150° C., 160° C. or 170° C. under the following conditions to obtain five kinds of dextrins in a combined amount of about 240 kg. These samples will hereinafter be designated by sample Nos. 1, 2, 3, 4 and 5, respectively.

Speed of rotation: 150 r.p.m. (two screws driven in the same direction)

Inlet temperature: room temp. (about 20° C.)

Maximum temperature: 170° C. (temp. of product at outlet)

Reaction time: 9 seconds

The indigestible component of each sample was quantitatively determined, and the sample was analyzed to determine the contents of glycosidic linkages thereof according to "Hakomori's methylation method". Detected by this procedure were a glucose residue at each non-reducing end, glucose residues having a 1→4 linkage, glucose residues having a 1→6 linkage, glucose residues having a 1→3 linkage, glucose residues each having both 1→4 linkage and 1→6 linkage, glucose residues each having both 1→3 linkage and 1→4 linkage, glucose residues each having both 1→2 linkage and 1→4 linkage, and glucose residues having other linkages. Table 4 shows the content of indigestible component and the values obtained by the analysis.

Incidentally, this method of quantitative determination involves errors which are usually about ±5% and which are inevitably at least ±2%.

TABLE 4

| Sample No. | Heating Temp. (°C.) | contents of linkages (%) | | | | | | | | Content of indigestible component (%) |
|---|---|---|---|---|---|---|---|---|---|---|
| | | Non-reducing end | 1→4 | 1→6 | 1→3 | 1→4, 1→6 | 1→3, 1→4 | 1→2, 1→4 | Others | |
| 1 | 130 | 25.7 | 53.6 | 5.9 | 2.9 | 7.1 | 1.2 | 1.8 | 1.8 | 53.3 |
| 2 | 140 | 28.6 | 40.3 | 10.8 | 5.3 | 8.7 | 1.0 | 2.2 | 3.1 | 69.4 |
| 3 | 150 | 31.5 | 31.0 | 12.9 | 8.5 | 7.8 | 0.9 | 2.3 | 5.1 | 75.6 |
| 4 | 160 | 32.6 | 22.0 | 14.6 | 11.1 | 6.8 | 1.1 | 2.6 | 9.2 | 84.2 |
| 5 | 170 | 32.5 | 15.0 | 16.8 | 13.2 | 6.6 | 1.1 | 2.8 | 12.0 | 90.1 |

Table 4 reveals the following. The content of indigestible component increases in proportion to the rise of temperature. Increases in proportion to the rise of temperature are also found in the amounts of glucose residues positioned at the non-reducing ends or having 1→6 glycosidic linkage, 1→3 glycosidic linkage, both 1→2 and 1→4 linkages, and in the amount of glucose residues having other linkages (listed as "Others" in Table 4, except the above residues, the residues having both 1→4 and 1→6 linkages and those having both 1→3 and 1→4 linkages).

The experiment demonstrates for the first time that only the amount of glucose residues having 1→4 linkage decreases in inverse proportion to the rise of temperature.

Next, the relation between the content indigestible component and the linkages listed in Table 4 was investigated by multi-regression analysis capable of determining the correlation between a multiplicity of variables to obtain equations and multi-correlation coefficients. The multi-regression analysis was conducted using the amounts of glucose residues having various glycosidic linkages as predictor variables and the content of indigestible component as criterion variable.

First, the correlation between the content of indigestible component and the amounts of glucose residues having various glycosidic linkages was investigated. Table 5 shows the coefficients A0, A1, A2, A3, A4, A5, A6, A7 and A8 of the equation and correlation coefficients obtained.

$$Y = A0 + An \cdot Xn$$

Wherein
Y: content of indigestible component (calculated value, %)
X1: amount (%) of glucose residues at the non-reducing end
X2: amount (%) of glucose residues having a 1→4 glycosidic linkage
X3: amount (%) of glucose residues having a 1→6 glycosidic linkage
X4: amount (%) of glucose residues having a 1→3 glycosidic linkage
X5: amount (%) of glucose residues having both 1→4 and 1→6 glycosidic linkages
X6: amount (%) of glucose residues having both 1.3→ and 1→4 glycosidic linkages
X7: amount (%) of glucose residues having both 1.2→ and 1→4 glycosidic linkages
X8: amount (%) of glucose residues having other glycosidic linkages

TABLE 5

| No. | Coefficient | | | | | | | | | correlation coefficient |
|---|---|---|---|---|---|---|---|---|---|---|
| | A0 | A1 | A2 | A3 | A4 | A5 | A6 | A7 | A8 | |
| 1 | −64.8 | 4.618 | — | — | — | — | — | — | — | 0.965 |
| 2 | 104.8 | — | −0.934 | — | — | — | — | — | — | 0.995 |
| 3 | 32.7 | — | — | 3.425 | — | — | — | — | — | 0.997 |
| 4 | 47.2 | — | — | — | 3.337 | — | — | — | — | 0.979 |
| 5 | 120.2 | — | — | — | — | −6.167 | — | — | — | 0.371 |
| 6 | 111.7 | — | — | — | — | — | −35.116 | — | — | 0.281 |
| 7 | −11.7 | — | — | — | — | — | — | 36.852 | — | 0.994 |
| 8 | 55.0 | — | — | — | — | — | — | — | 3.124 | 0.934 |

Consequently, of the eight kinds of glycosidic linkages, X5 (amount of glucose residues having both 1→4 and 1→6 glycosidic linkages) and X6 (amount of glucose residues having both 1→3 and 1→4 glycosidic linkages) were found to be very low in correlation coefficient (0.371 and 0.281 respectively for No 5 and No. 6 in Table 5), this indicating that the amounts of these glucose residues have no correlation with the content of indigestible component. Accordingly, multi-regression analysis was conducted to determine the relation between the content of indigestible component and the amounts of glucose residues having the following six types of glycosidic linkages other than the above two types of glycosidic linkages. For the 63 equations which are at least 0.9 in correlation coefficient and which are included in the equations obtained, Tables 6-1 to 6-3 show the following coefficients.

$$Y = A0 + A1 \cdot X1 + A2 \cdot X2 + A3 \cdot X3 + A4 \cdot X4 + A5 \cdot X5 + A6 \cdot X6$$

wherein
Y: content (%) of indigestible component (calculated value, %)
X1: amount (%) of glucose residues at the non-reducing end
X2: amount (%) of glucose residues having a 1→4 glycosidic linkage
X3: amount (%) of glucose residues having a 1→6 glycosidic linkage
X4: amount (%) of glucose residues having a 1→3 glycosidic linkage X5: amount (%) of glucose residues having 1→2 and 1→4 glycosidic linkages X6: amount (%) of glucose residues having glycosidic residues having both 1→4 and 1→6 glycosidic linkages and glycosidic residues having 1→3 and 1→4 glycosidic linkages

TABLE 6-1

| No. | A0 | A1 | A2 | A3 | A4 | A5 | A6 | Multi-correlation coefficient |
|---|---|---|---|---|---|---|---|---|
| 1 | −64.8 | 4.618 | — | — | — | — | — | 0.965 |
| 2 | 104.8 | — | −0.934 | — | — | — | — | 0.995 |
| 3 | 32.7 | — | — | 3.425 | — | — | — | 0.997 |
| 4 | 47.2 | — | — | — | 3.337 | — | — | 0.979 |
| 5 | −11.7 | — | — | — | — | 36.852 | — | 0.994 |
| 6 | 55.0 | — | — | — | — | — | 3.124 | 0.934 |
| 7 | 92.1 | 0.349 | −0.868 | — | — | — | — | 0.996 |
| 8 | 29.9 | 0.130 | — | 3.335 | — | — | — | 0.997 |
| 9 | 4.2 | 1.745 | — | — | 2.157 | — | — | 0.985 |
| 10 | −30.0 | 1.381 | — | — | — | 26.857 | — | 0.999 |
| 11 | −23.5 | 2.974 | — | — | — | — | 1.332 | 0.986 |
| 12 | 59.5 | — | −0.349 | 2.159 | — | — | — | 0.999 |
| 13 | 154.6 | — | −1.733 | — | −2.924 | — | — | 1.000 |
| 14 | 57.6 | — | −0.559 | — | — | 14.955 | — | 0.997 |
| 15 | 115.7 | — | −1.130 | — | — | — | −0.731 | 0.997 |
| 16 | 34.7 | — | — | 2.900 | 0.536 | — | — | 0.998 |
| 17 | 16.4 | — | — | 2.206 | — | 13.336 | — | 0.999 |
| 18 | 34.7 | — | — | 3.069 | — | — | 0.377 | 0.998 |
| 19 | −5.1 | — | — | — | 0.393 | 32.664 | — | 0.994 |
| 20 | 44.3 | — | — | — | 4.805 | — | −1.474 | 0.983 |
| 21 | −27.3 | — | — | — | — | 45.744 | −0.835 | 0.996 |

TABLE 6-2

| No. | A0 | A1 | A2 | A3 | A4 | A5 | A6 | Multi-correlation coefficient |
|---|---|---|---|---|---|---|---|---|
| 22 | 60.9 | −0.052 | −0.353 | 2.180 | — | — | — | 0.999 |
| 23 | 164.8 | −0.223 | −1.809 | — | −3.045 | — | — | 1.000 |
| 24 | −66.0 | 1.760 | 0.249 | — | — | 33.886 | — | 0.999 |
| 25 | 180.5 | −1.479 | −1.610 | — | — | — | −1.476 | 0.999 |
| 26 | 34.3 | 0.020 | — | 2.889 | 0.534 | — | — | 0.998 |
| 27 | −5.7 | 0.770 | — | 1.276 | — | 17.679 | — | 1.000 |
| 28 | 27.3 | 0.350 | — | 2.789 | — | — | 0.417 | 0.999 |
| 29 | −42.6 | 1.597 | — | — | −0.584 | 31.521 | — | 1.000 |
| 30 | −22.1 | 2.909 | — | — | 0.111 | — | 1.265 | 0.986 |
| 31 | −36.4 | 1.201 | — | — | — | 33.184 | −0.472 | 1.000 |
| 32 | 184.7 | — | −2.166 | −0.776 | −3.735 | — | — | 1.000 |
| 33 | 30.0 | — | −0.135 | 1.963 | — | 10.639 | — | 0.999 |
| 34 | 56.2 | — | −0.302 | 2.273 | — | — | 0.061 | 0.999 |
| 35 | 135.3 | — | −1.552 | — | −2.719 | 5.007 | — | 1.000 |
| 36 | 160.5 | — | −1.819 | — | −3.521 | — | 0.291 | 1.000 |
| 37 | 49.9 | — | −0.644 | — | — | 22.064 | −0.983 | 1.000 |
| 38 | 17.9 | — | — | 2.185 | 0.104 | 12.452 | — | 0.999 |
| 39 | 34.5 | — | — | 3.189 | −0.245 | — | 0.504 | 0.998 |
| 40 | 13.0 | — | — | 2.090 | — | 15.681 | −0.104 | 0.999 |
| 41 | −10.8 | — | — | — | 1.930 | 34.174 | −1.681 | 1.000 |
| 42 | 196.8 | −0.234 | −2.264 | −0.811 | −3.899 | — | — | 1.000 | sidic linkages other than the above residues, glyco-

TABLE 6-3

| No. | A0 | A1 | A2 | A3 | A4 | A5 | A6 | Multi-correlation coefficient |
|---|---|---|---|---|---|---|---|---|
| 43 | −39.6 | 1.132 | 0.233 | 1.258 | — | 24.371 | — | 1.000 |
| 44 | 797.3 | −8.856 | −8.090 | −11.209 | — | — | −9.100 | 0.999 |
| 45 | −17.5 | 1.005 | — | 1.066 | −0.363 | 22.089 | — | 1.000 |
| 46 | −17.7 | 2.298 | — | 3.100 | −3.813 | — | 2.613 | 1.000 |
| 47 | −17.5 | 0.869 | — | 0.851 | — | 24.420 | −0.275 | 1.000 |
| 48 | −17.3 | 0.323 | — | — | 1.451 | 33.667 | −1.373 | 1.000 |
| 49 | 105.1 | 0.293 | −1.294 | — | −2.381 | 9.397 | — | 1.000 |
| 50 | 152.4 | 0.284 | −1.795 | — | −3.870 | — | 0.535 | 1.000 |
| 51 | 28.9 | 0.314 | −0.489 | — | — | 24.497 | −0.852 | 1.000 |
| 52 | 156.6 | — | −1.840 | −0.460 | −3.236 | 4.127 | — | 1.000 |
| 53 | 177.0 | — | −2.056 | −0.452 | −3.890 | — | 0.240 | 1.000 |
| 54 | 55.2 | — | −0.768 | −0.491 | — | 24.591 | −1.183 | 1.000 |
| 55 | −32.7 | — | 0.232 | — | 2.626 | 38.544 | −1.933 | 1.000 |
| 56 | −17.5 | — | — | −0.522 | 2.323 | 39.320 | −2.035 | 1.000 |
| 57 | 16.0 | 0.810 | −0.354 | 0.773 | −0.916 | 18.622 | — | 1.000 |
| 58 | −17.7 | 2.506 | — | 3.427 | −4.368 | −3.553 | 3.034 | 1.000 |
| 59 | 65.4 | 0.304 | −0.874 | — | −1.142 | 17.260 | −0.443 | 1.000 |

TABLE 6-3-continued

| No. | Coefficient | | | | | | | Multi-correlation coefficient |
| --- | --- | --- | --- | --- | --- | --- | --- | --- |
| | A0 | A1 | A2 | A3 | A4 | A5 | A6 | |
| 60 | −47.0 | 1.221 | 0.311 | 1.394 | — | 24.356 | 0.092 | 1.000 |
| 61 | 11.3 | 1.955 | −0.306 | 2.571 | −3.822 | — | 2.259 | 1.000 |
| 62 | 73.4 | — | −0.959 | −0.485 | −0.580 | 20.917 | −0.970 | 1.000 |
| 63 | 23.1 | 2.110 | −0.430 | 2.819 | −4.611 | −5.023 | 2.710 | 1.000 |

In the multi-regression analysis using the six predictor variables, combinations of one to six predictor variables are 63 in total number. These 63 combinations are all at least 0.9 in multi-correlation coefficient. This indicates that there is a very close correlation between the amount of glucose residues having glycosidic linkages and the content of indigestible component.

Comparative Example 1

Preparation of dextrin by conventional process, structure of the dextrin and analysis of indigestible component A 5 kg portion of the remaining mixture of Experimental Example 1 was placed into a dryer and heated to 150° C. Five kinds of samples, each in an amount of 800 g, were collected from the heated mixture respectively 15 minutes, 30 minutes, 60 minutes, 120 minutes and 180 minutes after the start of heating.

The samples were analyzed similarly to determine the contents of glycosidic linkages thereof according to "Hakomori's methylation method". Detected by this procedure were glucose residues at the non-reducing ends, glucose residues having a 1→4 linkage, glucose residues having a 1→6 linkage, glucose residues each having both 1→4 linkage and 1→6 linkage, glucose residues each having both 1→3 linkage and 1→4 linkage, glucose residues each having both 1→2 linkage and 1→4 linkage, and glucose residues having other linkages. However, no 1→3 glycosidic linkage was detected by the experiment of this comparative example. Table 7 shows the detected values and the content of indigestible component.

TABLE 7

| Heating Time (min) | contents of linkages (%) | | | | | | | | Content of indigestible component (%) |
| --- | --- | --- | --- | --- | --- | --- | --- | --- | --- |
| | Non-reducing end | 1→4 | 1→6 | 1→3 | 1→4, 1→6 | 1→3, 1→4 | 1→2, 1→4 | Others | |
| 15 | 13.3 | 62.3 | 3.1 | — | 6.5 | 2.2 | 1.2 | 11.5 | 44.2 |
| 30 | 13.8 | 56.7 | 4.3 | — | 7.5 | — | 1.7 | 16.0 | 52.2 |
| 60 | 12.6 | 50.6 | 4.3 | — | 7.3 | 2.7 | 1.8 | 20.7 | 60.5 |
| 120 | 10.6 | 41.8 | 4.3 | — | 7.1 | 1.8 | 3.5 | 30.9 | 63.7 |
| 180 | 9.7 | 45.2 | 4.2 | — | 8.2 | 1.7 | 1.8 | 29.2 | 64.6 |

Table 7 shows the following. The content of indigestible component increases in proportion to the increase in heating time. The amount of glucose residues having 1→4 linkage decreases in inverse proportion to the increase in heating time, while the amount of glucose residues having other linkage increases in proportion to the increase in heating time, thus exhibiting a tendency similar to that of Table 4. However, the amount of glucose residues at the non-reducing ends decreases inverse-proportionally, and the amounts of glucose residues having 1→6 glycosidic linkage or both 1→2 and 1→4 glycosidic linkages have no correlation with the heating condition. In this respect, the result of Table 7 greatly differs from that of Table 4. This has been revealed by the present experiment for the first time.

Experimental Example 2

About 240 kg of a dextrin was prepared in the same manner as in Experimental Example 1 with the exception of adding 17.5 liters of 1% hydrochloric acid to 300 kg of commercial corn starch, treating the starch in the same manner as in Experimental Example 1 and thereafter heating the starch to 180° C. The product was analyzed in the same manner as in Experimental Example 1.

Experimental Example 3

About 240 kg of a dextrin was prepared in the same manner as in Experimental Example 1 with the exception of adding 17.5 liters of 1% hydrochloric acid to 300 kg of commercial corn starch, treating the starch in the same manner as in Experimental Example 1 and thereafter heating the starch to 160° C. The product was analyzed in the same manner as in Experimental Example 1. Table 8 shows the results of Experimental Example 2 and 3.

TABLE 8

| Exp. Example | contents of linkages (%) | | | | | | | | Content of indigestible component (%) |
| --- | --- | --- | --- | --- | --- | --- | --- | --- | --- |
| | Non-reducing end | 1→4 | 1→6 | 1→3 | 1→4, 1→6 | 1→3, 1→4 | 1→2, 1→4 | Others | |
| 2 | 29.6 | 38.7 | 11.3 | 6.0 | 7.4 | 1.1 | 2.2 | 3.7 | 70.6 |
| 3 | 30.4 | 15.0 | 17.1 | 12.7 | 7.4 | 1.0 | 2.7 | 13.7 | 90.4 |

The values listed in Table 8 were substituted in the equations 1 to 62 given in Table 6 to calculate content values of indigestible component, Y. Table 9 shows a summary of results as converted to values in percentage.

TABLE 9

| | Exp. Example | |
| --- | --- | --- |
| Item | 2 | 3 |
| Maximum variation range + (%) | 2.6 | 8.2 |
| Maximum variation range − (%) | −12.5 | −16.4 |
| Average variation range + (%) | 0.8 | 1.8 |
| Average variation range − (%) | −1.6 | −4.9 |
| Number of cases with variation range of over +15.1% | 0 | 0 |

TABLE 9-continued

| | Exp. Example | |
|---|---|---|
| Item | 2 | 3 |
| Number of cases with variation | 0 | 0 |

Similarly, the values listed in Table 7 were substituted in the equations 1 to 63 in Table 6 to calculate content values of indigestible component, Y. Table 10 shows a summary of results as converted to values in percentage.

TABLE 10

| | Heating time (min) | | | | |
|---|---|---|---|---|---|
| Item | 15 | 30 | 60 | 120 | 180 |
| Maximum variation range + (%) | 105.7 | 101.1 | 97.8 | 137.9 | 126.3 |
| Maximum variation range − (%) | −107.6 | −102.1 | −110.9 | −124.9 | −131.0 |
| Average variation range + (%) | 15.0 | 24.2 | 29.5 | 35.0 | 40.1 |
| Average variation range − (%) | −35.1 | −24.6 | −31.5 | −25.0 | −40.6 |
| Number of cases with variation range of over +15.1% | 5 | 9 | 11 | 28 | 13 |
| Number of cases with variation range of +10.1% to +15% | 6 | 2 | 2 | 7 | 1 |
| Number of cases with variation range of 0.1% to +10% | 11 | 5 | 1 | 5 | 1 |
| Number of cases with variation range of 0% | 0 | 0 | 0 | 0 | 0 |
| Number of cases with variation range of −0.1% to −10% | 8 | 18 | 6 | 3 | 4 |
| Number of cases with variation range of −10.1% to −15% | 3 | 2 | 5 | 6 | 1 |
| Number of cases with variation range of over −15.1% | 30 | 27 | 38 | 14 | 43 |
| Number of cases with variation range within ±5% | 11 | 8 | 3 | 3 | 3 |
| Number of cases with variation range within ±2% | 7 | 3 | 1 | 1 | 0 |

| | | |
|---|---|---|
| range of +10.1% to +15% | | |
| Number of cases with variation range of 0.1% to +10% | 16 | 25 |
| Number of cases with variation range of 0% | 1 | 1 |
| Number of cases with variation range of −0.1% to −10% | 44 | 35 |
| Number of cases with variation range of −10.1% to −15% | 1 | 0 |
| Number of cases with variation range of over −15.1% | 0 | 1 |
| Number of cases with variation range within ±5% | 61 | 42 |
| Number of cases with variation range within ±2% | 50 | 25 |

With reference to Table 9, Experimental Example 2 by extruder, all the 62 cases were within the range of ±15% in the variation of the calculated value Y from the actual measurement, and these cases included 61 cases wherein the range was within ±10%. The variation was outside the range of ±15% in none of the cases. The variation was within ±5% in 61 cases and within ±2% in 50 cases.

In Experimental Example 3, 61 cases were within the range of ±15% in the variation of the calculated value Y from the actual measurement, and in all of these 61 cases, the range was within ±10%. The variation was outside the range of ±15% in 1 case. The variation range was within ±5% in 42 cases and within ±2% in 25 cases. These results indicate that the relational equation in Table 6 are very high in correlation between the glycosidic linkages of the dextrin and the content of indigestible component thereof.

With reference to Table 10 showing the results achieved by the samples of dextrin prepared by the conventional process, the samples were extremely great in variation range and had little or no correlation with the equations of Table 6. This indicates that the difference in heating process resulted in a great difference in the structure of product.

Comparative Example 2

About 230 kg of a dextrin was prepared in the same manner as in Experimental Example 1 with the exception of adding 22.5 liters of 1% hydrochloric acid to 300 kg of commercial potato starch, treating the starch in the same manner as in Experimental Example 1 and thereafter heating the starch to 140° C. The product was analyzed in the same manner as in Experimental Example 1.

Comparative Example 3

About 240 kg of a dextrin was prepared in the same manner as in Experimental Example 1 with the exception of adding 22.5 liters of 1% hydrochloric acid to 300 kg of commercial tapioca starch, treating the starch in the same manner as in Experimental Example 1 and thereafter heating the starch to 140° C. The product was analyzed in the same manner as in Experimental Example 1. Table 11 shows the results of analysis obtained in Comparative Examples 2 and 3.

TABLE 11

| Comp. Example | contents of linkages (%) | | | | | | | | Content of indigestible component (%) |
|---|---|---|---|---|---|---|---|---|---|
| | Non-reducing end | 1→4 | 1→6 | 1→3 | 1→4, 1→6 | 1→3, 1→4 | 1→2, 1→4 | Others | |
| 2 | 26.9 | 39.1 | 9.7 | 6.9 | 9.1 | 1.4 | 2.9 | 4.0 | 75.0 |
| 3 | 16.8 | 58.3 | 4.4 | 3.5 | 10.9 | 1.5 | 2.4 | 3.2 | 54.7 |

The results obtained by analyzing the products of the above two comparative examples were substituted in the equation 63 wherein all the six variables were used to calculate the content values of indigestible component. Table 12 shows the calculated values in comparison with the actual measurements.

TABLE 12

| | Indigestible component | | |
|---|---|---|---|
| Comp. Example | Measured (%) | Calculated (%) | Range of variation from measurement (%) |
| 2 | 75.0 | 55.4 | −26.1 |
| 3 | 54.7 | 26.8 | −51.0 |

Table 12 shows that even if heat-treated by the same process, different material starches afford products which are greatly different in structure.

Experimental Example 4

Eleven samples of the dextrins prepared in Experimental Examples 1, 2, 3 and Comparative Example 1 were checked for the degree of coloration by measuring the whiteness of the samples relative to the whiteness of magnesium oxide taken as 100%, using photoelectric whiteness meter (product of Kett Co.) and a blue filter. Table 13 shows the results.

TABLE 13

| Sample | | | Whiteness (%) |
|---|---|---|---|
| Exp. Ex. 1 | Heating Temp. | 130° C. | 66.0 |
| | | 140° C. | 50.5 |
| | | 150° C. | 40.5 |
| | | 160° C. | 35.8 |
| | | 170° C. | 21.2 |
| Exp. Ex. 2 | Heating Temp. | 180° C. | 20.5 |
| Exp. Ex. 3 | Heating Temp. | 160° C. | 37.1 |
| Comp. Ex. 1 Heating Temp. 150° C. | Heating time | 15 min | 29.7 |
| | | 30 min | 21.5 |
| | | 60 min | 18.4 |
| | | 120 min | 15.8 |
| | | 180 min | 12.3 |

The whiteness decreased generally in inverse proportion to the heating temperature or heating time. However, the whiteness of comparative example 1 is such lower that of the products of present invention. This reveals that the conventional products were not practically useful.

Experimental Example 5

Sample Nos. 1, 2, 3, 4 and 5 were checked for the content of dietary fiber and caloric values as determined by the foregoing two measuring methods. Table 14 shows the results along with the content of indigestible component.

TABLE 14

| Sample No. | Indigestible content (%) | Component of dietary fiber (%) | Caloric value 1 Kcal/g | Caloric value 2 Kcal/g |
|---|---|---|---|---|
| 1 | 53.3 | 8.8 | 2.73 | 2.40 |
| 2 | 69.4 | 17.7 | 2.35 | 1.92 |
| 3 | 75.6 | 23.3 | 2.20 | 1.73 |
| 4 | 84.2 | 30.8 | 2.00 | 1.47 |
| 5 | 90.1 | 36.5 | 1.86 | 1.30 |

The values given in Table 14 appear to indicate that the dietary fiber content is in proportional relation with the content of indigestible component and is in inversely proportional relation with the caloric values. Accordingly, the correlation of the content of indigestible component with the dietary fiber content and with the caloric values was determined by the least square method to obtain Equation 64 as to the dietary fiber content, Equation 65 as to the caloric value 1 and Equation 66 as to the caloric value 2.

$$Y_1 = 14.29 - 0.1675 \cdot I - 0.01091 \cdot I^2 + 3.067 \cdot 10^{-4} \cdot I^3 - 1.494 \cdot 10^{-6} \cdot I^4 \quad (64)$$

$$Y_2 = 3.99 - 0.0236 \cdot I \quad (65)$$

$$Y_3 = 3.99 - 0.02998 \cdot I \quad (66)$$

wherein
- $Y_1$: dietay fiber content (clculated value, %)
- $Y_2$: caloric value 1 (calculated value, kcal/g)
- $Y_3$: caloric value 2 (calculated value, kcal/g)
- $I$: content of indigestible component (analyzed value, %)

Next, the content of indigestible component was substituted in these three equations. Tables 15, 16 and 17 show the calculated values obtained in comparison with measured values.

TABLE 15

| Sample No. | Content of dietary fiber (%) | | Difference between calculated value and measurement (%) | |
|---|---|---|---|---|
| | Measured | Calculated | Difference | Variation ratio |
| 1 | 8.8 | 8.8 | 0.0 | 0.0 |
| 2 | 17.7 | 18.0 | 0.3 | 1.7 |
| 3 | 23.3 | 23.0 | −0.3 | −1.3 |
| 4 | 30.8 | 30.8 | 0.0 | 0.0 |
| 5 | 36.5 | 36.5 | 0.0 | 0.0 |

TABLE 16

| Sample No. | Caloric value 1 (Kcal/g) | | Difference between calculated value and measurement (%) | |
|---|---|---|---|---|
| | Measured | Calculated | Difference | Variation ratio |
| 1 | 2.73 | 2.73 | 0.00 | 0.0 |
| 2 | 2.35 | 2.35 | 0.00 | 0.0 |
| 3 | 2.20 | 2.21 | 0.01 | 0.5 |
| 4 | 2.20 | 2.00 | 0.00 | 0.0 |
| 5 | 1.86 | 1.86 | 0.00 | 0.0 |

TABLE 17

| Sample No. | Caloric value 2 (Kcal/g) | | Difference between calculated value and measurement (%) | |
|---|---|---|---|---|
| | Measured | Calculated | Difference | Variation ratio |
| 1 | 2.40 | 2.40 | 0.00 | 0.0 |
| 2 | 1.92 | 1.92 | 0.00 | 0.0 |
| 3 | 1.73 | 1.73 | 0.00 | 0.0 |
| 4 | 1.47 | 1.48 | 0.01 | 0.7 |
| 5 | 1.30 | 1.30 | 0.00 | 0.0 |

The calculated values given in Tables 15 to 17 are well in match with the respective measured values. This demonstrates a close relation of the content of indigestible content with the dietary fiber content as well as with the caloric values.

Next, investigations were made to determine the physiological activities of the indigestible dextrin of the invention using commercial white dextrin and samples Nos. 3 and 5 of Experimental Example 1. These three samples will hereinafter be referred to as "samples A, B and C," respectively.

Experimental Example 6

Animal Experiment

Male rats of Sprague-Dawley strain (6 rats/group) initially weighing about 50 g were accommodated in individual cages placed in a small animal breeding chamber controlled to 23°±2° C., preliminarily raised with a commercial synthetic diet for 1 week, and thereafter fed for 7 days with a basal diet, or the basal diet containing 5% of the sample A, B or C added thereto, or the basal diet containing 5% cellulose (Avicel, product of Sanyo-Kokusaku Pulp Co., Ltd.) with free access to water and the diet. The intake of diet and changes in body weight were recorded daily. On the seventh day, carmine (pigment) was given as admixed with the diet, and the time taken for the carmine to appear in feces was measured as transit time. The animals were thereafter sacrificed with blood taken, and the cecum was removed and checked for the weight thereof, pH of the contents of the cecum and the amount of butyric acid therein. Table 18 shows the average values of results obtained.

TABLE 18

| | Weight of cecum (g) | Contents of cecum (pH) | Amount of butyric acid (mg/cecum) | Excretion time (hr) |
|---|---|---|---|---|
| Basal diet | 1.2 | 8.0 | 4.0 | 13.2 |
| Basal diet + Sample A | 4.0 | 6.4 | 16.0 | 10.4 |
| Basal diet + Sample B | 4.5 | 5.9 | 25.2 | 8.2 |
| Basal diet + Sample C | 5.1 | 5.8 | 26.3 | 8.2 |
| Basal diet + cellulose | 2.5 | 7.6 | 14.3 | 8.2 |

The results listed in Table 18 reveal that the sample A, B or C reached the large intestine while remaining indigested, metabolized to organic acids under the action of enterobacteria and resulted in a lower pH within the intestine. While the ingestion of any of the samples A, B and C shortened the transit time, comparison with the group receiving cellulose, which is effective for improved defecation, indicated that the samples B and C were effective. Accordingly, the sample B was further used for clinical tests to substantiate its effect.

Experimental Example 7

Clinical Test

The sample B was given at a daily dose of 10 g to ten males in good health during a test period of 2 weeks. During the first and second weeks of the test period, they are given the same meals in same quantities, and the sample was administered after breakfast on Monday through Friday. Feces were collected on every defecation and checked for wet weight, dry weight, water content and frequency of defecation. Table 19 shows the results obtained. The values listed are mean values, and the mark * indicates a significance level of 5% relative to the non-ingestion period, hence a significant difference.

TABLE 19

| Test period | Non-ingestion period | Ingestion period |
|---|---|---|
| Wet weight of feces | 535 g | 782 g* |
| Dry weight of feces | 111 g | 166 g* |
| Amount of water in feces | 430 g | 620 g* |
| Water content of feces | 76.5% | 77.7% |
| Frequency of excretion | 4.5 times | 5.8 times* |

The results of Table 19 reveal that the sample has an effect to increase the overall amount of feces.

Experimental Example 8

Clinical Test

The sample B was checked for a constipation alleviating effect. The sample was given to 25 volunteers having a tendency toward constipation at a predetermined dose for at least 5 days. Changes resulting from the administration of the sample in defecation were checked with a questionnaire. Scores are assigned to the checked items on the questionnaire according to the following criteria to substantiate the effect through a statistical procedure.

(1) Frequency of excretion
At least once/day: score 4
Once/day: score 3
Once/two days: score 2
Once/three days: score 1
(2) Amount of excretion
Large: score 4
Usual: score 3
Small: score 2
None: score 1
(3) State of feces
Bananalike, pasty: score 2
Hard: score 1
(4) Feeling after defecation
Complete discharge: score 2
Incomplete discharge: score 1

Table 20 shows the results. The mark * listed indicates a significance level of 5% relative to "before administration," hence a significant difference.

TABLE 20

| | Amount administered | |
|---|---|---|
| | 5 g | 10 g |
| Before administration | 8.50 | 8.43 |
| After administration | 11.00* | 12.20* |

With reference to Table 20, the sample B, when administered at a dose of at least 5 g, resulted in increased scores and was found effective for alleviating constipation.

Experimental Example 9

Animal Test

Rats were used for a nutritional experiment to check the samples A, B and C for a serum lipid lowering effect.

Male rats of Sprague-Dawley strain initially weighing about 50 g (3-week-old, provided by CLEA Japan Co.) were preliminarily raised for two weeks on a high-sucrose diet (basal diet) shown in Table 21, and thereafter raised and divided into five groups (10 rats in each group) for 9 weeks, during which the basal diet was given to the first group (control group), and a test diet comprising 95% of the basal diet and 5% of the sample A, B or C admixed therewith was given the second group (sample A group), third group (sample B group) and fourth group (sample C group), with free access to the diet and water.

TABLE 21

| Material | Weight parts |
|---|---|
| Casein | 25 |
| Corn oil | 5 |
| Salt (MM-2) mixture | 4 |
| Vitamin (Harper) mixture | 1 |
| Choline chloride | 0.2 |

TABLE 21-continued

| Material | Weight parts |
|---|---|
| Vitamin E | 0.05 |
| Sucrose | 64.75 |

In the 9th week, the rats were fasted for 4 hours, blood was then taken, and the serum total cholesterol value and neutral fat value thereof were determined by a kit for enzyme method (product of Wako Junyaku Co., Ltd.). Table 22 shows the results.

TABLE 22

| Item | Group | | | |
|---|---|---|---|---|
| | 1st | 2nd | 3rd | 4th |
| Weight gain (g/9 weeks) | 298 | 288 | 288 | 285 |
| Diet efficiency | 0.25 | 0.25 | 0.25 | 0.25 |
| Serum total cholesterol | 121 | 70 | 68 | 67 |
| Serum neutral fat | 275 | 153 | 129 | 129 |

The results achieved by the test groups are expressed in mean values. The diet efficiency was calculated from Equation 67.

$$\text{Diet efficiency} = \text{weight gain} \div \text{diet intake} \qquad 67$$

As seen from Table 22, there was no difference between the three sample groups in weight gain and diet efficiency. However, the sample A, B and C groups were apparently lower in serum total cholesterol value and neutral fat value than the control group. The samples B and C were found to be remarkably effective. Accordingly, sample B was further tested clinically Experimental Example 10

Clinical Test

Sample B (10 g) was dissolved in 100 ml of water, and the solution was orally administered to 10 persons three times a day before every meal for four weeks, during which they observed usual eating habits and were allowed to perform routine work. The persons participating in the test were 34 to 61 years old (53.3 on the average age), 159 to 171 cm tall (166.8 cm on the average) and weighed 53 to 81 kg (64.8 kg on the average). Table 23 shows the results obtained as expressed in the unit of mg/dl.

TABLE 23

| Item | Normal value | Before administration | After administration |
|---|---|---|---|
| Total cholesterol | 120~250 | 232 | 188 |
| HDL-cholesterol | 40~65 | 46 | 49 |
| Neutral fat | 67~172 | 244 | 165 |

Table 23 reveals that the administration of the sample B altered the serum total cholesterol value toward the normal value (120~250 mg/dl). Those who were higher than the normal in this value exhibited a reduction. As similar result was observed also with respect to the neutral fat value. These results substantiate that the sample B has a remarkable effect in improving serum lipid metabolism.

Experimental Example 11

Insulin

An experiment conducted with 36 rats revealed that the blood sugar value of 78.0 mg/dl on average and the insulin secretion of 17.3 $\mu$U/ml on average, when the rats were hungry, increased to the highest levels of 164 mg/dl and 49.9 $\mu$U/dl on average, respectively, 30 minutes after sugar was orally given to the rats in an amount of 1.5 g/kg body weight, and lowered to the respective normal values 120 minutes thereafter. However, addition of the sample B to the sugar in an amount of 0.15 to 1.5 g (in a proportion of 1/10 to 1/1 to the amount of sugar) resulted in smaller increases 30 minutes after administration; the average blood sugar value and the average value of insulin secretion thereby increased and were 144 mg/dl and 32.3 $\mu$U/ml, respectively, when the proportion was 1/10 and 138 mg/dl and 31.1 $\mu$U/ml, respectively, when the proportion was 1/1. This indicates that the indigestible dextrin significantly suppresses the rise of blood sugar value and insulin secretion due to sugar.

Incidentally, when 0.15 g of sample A was similarly added to the sugar, the blood sugar value increased to 169 mg/dl on average 30 minutes later, i.e., to the same level as when sugar only was orally administered.

Summary of Experimental Data as Analyzed

To sum up the results obtained by analyzing the foregoing experimental data, the dextrin of the invention prepared by heating starch in an extruder greatly differs from the dextrin of the prior art with respect to the following in the case where the content of indigestible component is at lest 60%.

(1) The content of indigestible component is 90% at the maximum.
(2) The content of glucose residues having 1→4 glycosidic linkage is about 15% to about 50%, whereas the corresponding value of the prior art is at least about 60%.
(3) The content of glucose residues having 1→6 glycosidic linkage is about 8 to about 17% maximum, whereas the corresponding value of the prior art is only 4%.
(4) The content of glucose residues having 1→3 glycosidic linkage is about 4 to 13% in contrast to only traces of these residues found in the conventional product.
(5) The content of glucose residues having other glycosidic linkages is about 2 to about 12%, whereas the corresponding value of the prior art is at least about 20%.
(6) The contents of glucose residues having various glycosidic linkages other than those having the above linkages, 1→4 and 1→6 glycosidic linkages and 1→3 and 1→4 glycosidic linkages are in close correlation with the content of indigestible component.
(7) Among the 63 equations, the equation 63 including all the six predictor variables represents the closest relationship between the whole of glycosidic linkages and the content of indigestible component involved in the present dextrin which is prepared by adding hydrochloric acid to corn starch and then heating the starch by an extruder. The content value of indigestible component obtained by similarly heating a starch other than corn starch, i.e., potato starch or tapioca starch, with addition of an acid using an extruder, analyzing the heat-treated starch to determine the contents of glycosidic linkages thereof and substituting the content values in the equation 63 is greatly different from actual measurement. Apparently, therefore, the equation is applicable specifically to corn starch only.

(8) As the heating temperature rises, the product contains a larger amount of colored substance, resulting in the whiteness level lowering to about 20% which is considered to be the lower limit for use of the product as a food material. Thus, the heating temperature is limited for the use of the product.

The above experimental results indicate that the dextrin of the present invention is a novel substance which has a higher content of indigestible component than the dextrin obtained by the conventional heat treatment process and which distinctly differs from the conventional product in structure.

(9) It has been further found that the content of indigestible component has a close correlation with the dietary fiber content and also with the caloric value.

(10) Furthermore, the indigestible dextrin, when ingested, is found effective for improving the internal environment of the intestine and eliminating constipation and diarrhea by giving a lower pH to the interior of the intestine and increasing the amounts of short-chain fatty acids having an intestine conditioning effect.

(11) The dextrin further acts to diminish cholesterol and neutral fats among other serum lipids, consequently preventing arterial sclerosis and hypertension.

(12) The dextrin further has an effect to reduce the rise of blood sugar and insulin secretion after meals.

(13) Because of these effects, the indigestible dextrin of the present invention is very useful as a material for alimentotherapy to accomplish the above purposes.

In one embodiment of the present invention, the indigestible dextrin can be up to 2.6 kcal/g in caloric value 1 and up to 2.2 kcal/g in caloric value 2. In an embodiment of the present invention when the indigestible dextrin contains up to 40% of 1→4 glycosidic linkages and at least 70% of indigestible component, the indigestible dextrin can be up to 2.3 kcal/g in caloric value 1 and up to 1.9 kcal/g in caloric value 1.

Next, as to the heating condition for the extruder, it is desirable to use a high temperature to give an increased content of indigestible component as is apparent from Table 1. To obtain a product with an indigestible content of at least 60%, the treatment is conducted at a temperature of at least about 130° C., preferably at least 140° C. The product can then be 70% or higher in content. However, the treatment may be conducted at a relatively low temperature when a large-sized extruder is employed because the reaction time is then longer owing to the structure of the apparatus.

Although the progress of the reaction is controllable by using an increased amount of acid, but presence of a large excess of acid causes corrosion or abrasion to the extruder. Accordingly, it is suitable to use up to 3,000 ppm, more preferably about 1,000 ppm, of acid based on the starch material.

The product as heat-treated by the extruder contains hydrochloric acid and therefore needs to be neutralized and thereafter refined, for example, by decoloration with activated carbon, filtration and desalting with ion exchange resin when to be used for purposes other than feeds. However, if the material starch is heated in the extruder at high temperatures over 180° C., an increased amount of colored substance will result to impair the quality of the product in spite of neutralization and purification. The product is accordingly undesirable for use in foods.

Further, the product to be refined can be hydrolyzed with alpha-amylase and thereby given a reduced viscosity. This also permits more efficient refining. The refined product can be given a higher content of indigestible component by being subjected to continuous chromatography with use of an ion exchange resin of the alkali metal or alkaline earth metal type to separate off the digestible component.

EXAMPLE

Examples of the invention are given below.

Example 1

Commercial corn starch (500 kg) was placed into a ribbon mixer, and 50 liters of 1% hydrochloric acid solution was sprayed onto the starch by pressurized air while rotating the mixer. The mixture then passed through a disintegrator to obtain a uniform mixture, which was further treated in the ribbon mixer for 1 hour. The mixture was pre-dried to a water content of about 6% by a flash dryer, subsequently continuously charged into a twin-screw extruder (Model TEX-52FSS-20AW-V for foods, manufactured by Japan Steel Works, Ltd. and having screws rotative in the same or different directions on change-over, 52 mm in diameter and 20/1 in length/diameter, drive motor 7.5 KW in output and rotatable at 400 r.p.m. max., aluminum cast heater, water cooling system with vent hole) and heat-treated under the following conditions to obtain about 400 kg of indigestible dextrin with moisture content of 2.0%.

Speed of rotation: 150 r.p.m., two screws rotated in the same direction
Inlet temperature: room temp. (about 20° C.)
Heating temperature: 150° C. (temp. of product at outlet)
Reaction time: 9 seconds

Example 2

Commercial corn starch (500 kg) was placed into a ribbon mixer, and 35 liters of 1% hydrochloric acid solution was sprayed onto the starch by pressurized air while rotating the mixer. The mixture then passed through a disintegrator to obtain a uniform mixture, which was further treated in the ribbon mixer for 1 hour. The mixture was pre-dried to a water content of about 6% by a flash drier, subsequently continuously charged into the same twin-screw extruder as in Example 1 and heat-treated under the following conditions to obtain about 400 kg of indigestible dextrin with moisture content of 1.8%.

Speed of rotation: 150 r.p.m., with two screws rotated in the same direction
Inlet temperature: room temp. (about 20° C.)
Heating temperature: 200° C. (temp. of product at outlet)
Reaction time: 7 seconds

Example 3

Commercial corn starch (500 kg) was placed into a ribbon mixer, and 75 liters of 1% hydrochloric acid solution was sprayed onto the starch by pressurized air while rotating the mixer. The mixture then passed through a disintegrator to obtain a uniform mixture, which was further treated in the ribbon mixer for 1 hour. The mixture was pre-dried to a water content of about 6% by a flash dryer, subsequently continuously charged into the same twin-screw extruder as in Example 1 and heat-treated under the following conditions to obtain about 400 kg of indigestible dextrin with moisture content of 2.4%.

Speed of rotation: 135 r.p.m., with two screws rotated in the same direction
Inlet temperature: room temp. (about 20° C.)
Heating temperature: 140° C. (temp. of product at outlet)
Reaction time: 30 seconds

Example 4

Commercial corn starch (2,500 kg) was placed into a ribbon mixer, and 38 liters of 1% hydrochloric acid solution was sprayed onto the starch by pressurized air while rotating the mixer. The mixture then passed through a disintegrator to obtain a uniform mixture, which was further treated in the ribbon mixer for 1 hour. The mixture was pre-dried to a water content of about 5.5% by a flash dryer, subsequently continuously charged into a twin-screw extruder (Model TEX-95FC-23AW-2V for foods, manufactured by Japan Steel Works, Ltd. and having screws rotative in the same direction, 95 mm in diameter and 23/1 in length/diameter, drive motor 132 KW in output and rotatable at 300 r.p.m. max., aluminum cast heater, water cooling system and two vent holes) and heat-treated under the following conditions to obtain about 2,100 kg of indigestible dextrin with moisture content of 2.3%.

Speed of rotation: 180 r.p.m.
Inlet temperature: room temp. (about 20° C.) Heating temperature: 170°~180° C. (temp. of product at outlet)
Reaction time: 14.5 seconds

Example 5

Commercial corn starch (2,500 kg) was dried by a flash dryer to a water content of 5% and then placed into a ribbon mixer, and 178 liters of 1% hydrochloric acid solution was sprayed onto the starch by pressurized air while rotating the mixer. The mixture then passed through a disintegrator to obtain a uniform mixture, which was further treated in the ribbon mixer for 1 hour. The mixture was continuously charged into the same twin extruder as used in Example 4 and heat-treated under the following conditions to obtain about 2,200 kg of indigestible dextrin with moisture content of 2.7%.

Speed of rotation: 180 r.p.m.
Inlet temperature: room temp. (about 20° C.)
Heating temperature: 150°~160° C. (temp. of product at outlet)
Reaction time: 12.5 seconds The indigestible dextrins prepared from corn starch in Examples 1 to 5 were similarly analyzed by "Hakomori's methylation method" to determine contents of various glycosidic linkages and contents of indigestible components. Table 24 shows the results collectively.

TABLE 24

| Example No. | contents of linkages (%) | | | | | | | | Content of indigestible component (%) |
|---|---|---|---|---|---|---|---|---|---|
| | Non-reducing end | $1 \to 4$ | $1 \to 6$ | $1 \to 3$ | $1 \to 4, 1 \to 6$ | $1 \to 3, 1 \to 4$ | $1 \to 2, 1 \to 4$ | Others | |
| 1 | 32.6 | 14.1 | 17.1 | 13.7 | 6.4 | 1.0 | 2.8 | 12.3 | 92.5 |
| 2 | 31.5 | 25.5 | 13.9 | 10.5 | 7.4 | 1.1 | 2.5 | 7.6 | 80.6 |
| 3 | 30.2 | 33.7 | 11.7 | 8.1 | 8.1 | 1.0 | 2.3 | 4.9 | 71.7 |
| 4 | 32.0 | 15.9 | 15.2 | 11.7 | 7.7 | 1.0 | 2.8 | 13.7 | 94.5 |
| 5 | 30.7 | 28.8 | 12.4 | 8.5 | 8.5 | 1.1 | 2.5 | 7.5 | 78.8 |

Next, the values given in Table 24 were substituted in the equations 1 to 62 listed in Table 6 to calculate contents Y of indigestible components. The results are summarized in Table 25 in terms of percent values.

TABLE 25

| Item | Example | | | | |
|---|---|---|---|---|---|
| | 1 | 2 | 3 | 4 | 5 |
| Maximum variation range + (%) | 1.0 | 8.0 | 13.6 | 3.5 | 8.1 |
| Maximum variation range − (%) | −7.3 | −4.2 | −3.2 | −15.0 | −6.0 |
| Average variation range + (%) | 0.7 | 1.3 | 2.5 | 1.1 | 1.8 |
| Average variation range − (%) | −2.0 | −0.9 | −2.4 | −6.5 | −2.3 |
| Number of cases with variation range of over +15.1% | 0 | 0 | 0 | 0 | 0 |
| Number of cases with variation range of +10.1% to +15% | 0 | 0 | 1 | 0 | 0 |
| Number of cases with variation range of 0.1% to +10% | 2 | 24 | 57 | 6 | 26 |
| Number of cases with variation range of 0% | 0 | 3 | 0 | 0 | 2 |
| Number of cases with variation range of −0.1% to −10% | 60 | 35 | 4 | 49 | 34 |
| Number of cases with variation range of −10.1% to −15% | 0 | 0 | 0 | 7 | 0 |
| Number of cases with variation range of over −15.1% | 0 | 0 | 0 | 0 | 0 |
| Number of cases with variation range within ±5% | 61 | 61 | 58 | 23 | 60 |
| Number of cases with variation range within ±2% | 29 | 54 | 32 | 13 | 37 |

With reference to Table 25, none of the five examples are outside the range of ±15% in the variation of the calculated value Y from the actual measurement. With respect to these examples, 55 to 62 cases among all the 62 cases are within the range of ±10%, 23 to 61 cases are within the range of ±5%, and 13 to 54 cases are within the range of ±2%. These results indicate that the equations of Table 6 represent a very high correlation and are also applicable to the examples.

Next, the results of the examples listed in Table 24 were substituted in Equation 63 to calculate the contents of indigestible components, which are shown in Table 26 in comparison with the corresponding measurements.

TABLE 26

| Example | Indigestible component | | |
|---|---|---|---|
| | Measured (%) | Calculated (%) | Range of variation from measurement (%) |
| 1 | 92.5 | 90.1 | −2.6 |
| 2 | 80.6 | 77.4 | −4.0 |
| 3 | 71.7 | 69.7 | −2.8 |
| 4 | 94.5 | 95.7 | +1.3 |
| 5 | 78.8 | 79.0 | +0.3 |

The variations of the calculated values from the measurements were in the range of +1.3% to −4.0%.

Similarly, the measured values of indigestible components of the examples were substituted in Equation 64 to calculate dietary fiber contents, which are shown in Table 27 in comparison with the measurements.

TABLE 27

| Example | Content of dietary fiber | | |
|---|---|---|---|
| | Measured (%) | Calculated (%) | Range of variation from measurement (%) |
| 1 | 40.1 | 38.8 | −3.2 |
| 2 | 26.8 | 27.5 | +2.6 |
| 3 | 19.4 | 19.8 | +2.1 |
| 4 | 42.5 | 40.7 | −4.2 |
| 5 | 25.3 | 25.8 | +2.0 |

Similarly, the measured values of indigestible components were substituted in Equation 65 to calculate caloric values 1, which are shown in Table 28 in comparison with the measurements.

TABLE 28

| Example | Caloric value-1 | | |
|---|---|---|---|
| | Measured (%) | Calculated (%) | Range of variation from measurement (%) |
| 1 | 1.80 | 1.81 | +0.5 |
| 2 | 2.08 | 2.09 | +0.5 |
| 3 | 2.29 | 2.30 | +0.4 |
| 4 | 1.79 | 1.76 | −1.7 |
| 5 | 2.11 | 2.13 | +0.9 |

Similarly, the measured values of indigestible components of the examples were substituted in Equation 66 to calculate caloric values 2, which are shown in Table 29 in comparison with the measurements.

TABLE 29

| Example | Caloric value-2 | | |
|---|---|---|---|
| | Measured (%) | Calculated (%) | Range of variation from measurement (%) |
| 1 | 1.23 | 1.22 | −0.8 |
| 2 | 1.57 | 1.57 | −0.0 |
| 3 | 1.85 | 1.84 | −0.5 |
| 4 | 1.12 | 1.16 | +3.6 |
| 5 | 1.60 | 1.63 | +1.9 |

With reference to Tables 27 to 29, the variations of the calculated values from the measurements are within the range of about 4%. This indicates that the values have a close correlation with the contents of indigestible components.

Example 6

A 2,000 kg quantity of the indigestible dextrin of Example 4 was dissolved in 4,000 liters of water, the solution neutralized to a pH of 5.8 with 1N aqueous solution of sodium hydroxide, 4 kg of TERMAMYL 60L (liquid alpha-amylase, product of NOVO Industry Co., Ltd.) added to the solution, and the mixture was heated to about 95° C. for 15 minutes in an autoclave for hydrolysis. Next, fresh steam was introduced into the autoclave to heat the hydrolyzate, which was autoclaved at 125° C. for 3 minutes and then discharged into the atmosphere. 4 kg of TERMAMYL 60L was added again to the hydrolyzate as it cooled to a temperature of 85° C., followed by further hydrolysis for 20 minutes, introduction of fresh steam and autoclaving. The resulting hydrolyzate was discharged to the atmosphere, cooled to about 80° C., decolorized with activated carbon, filtered and subsequently desalted with a mixed bed of ion exchange resin, followed by decoloration with active carbon and filtration again. The filtrate was concentrated in a vacuum to a concentration of about 50% and then spray-dried, giving about 1,600 kg of refined indigestible dextrin with moisture content of 2.2%.

Example 7

A 2,000 kg quantity of the dextrin of Example 5 was dissolved in 4,000 liters of water, and the solution was neutralized to a pH of 5.8 with 1N aqueous solution of sodium hydroxide, heated in an autoclave with fresh steam introduced thereinto, autoclaved at 130° C. for 2 minutes, then discharged into the atmosphere and cooled to about 80° C. The resulting product was decolorized with active carbon, filtered, desalted with a mixed bed of ion exchange resin, decolored with active carbon again and filtered. The filtrate was concentrated in a vacuum to a concentration of about 50% and thereafter spray-dried, giving about 1,650 kg of refined indigestible dextrin with moisture content of 3.1%.

The indigestible dextrin of the present invention is usable for almost all foods. The term "foods" as used herein refers collectively to foods for man and feeds for livestock and for use in zoos and for pets. The indigestible dextrin is prepared from starch, is soluble in water, contains dietary fiber, and is usable also as a low calorie bulking agent in foods, so that it is usable in any food wherein dextrin and maltodextrin are usually usable. More specifically, the indigestible dextrin is effectively usable for liquid or powdery beverages such as coffee, black tea, cola and juice; baked products such as bread, cookies, crackers, cakes, pizza and pies; noodles such as wheat noodles, Chinese noodles and buckwheat noodles; pasta such as spaghetti, macaroni and fettuccine; confectionery such as candies, chocolate and chewing gum; doughnut, potato chips and like fried cakes or foods; ices such as ice cream, shakes and sherbets; daily products such as cream, cheese, milk powder, condensed milk, creamy powder, coffee whitener and milk beverages; chilled desserts such as custard pudding, yoghurt, drinkable yoghurt, jelly, mousse and Bavarian; retorted pouched or canned foods such as soups, stew, gratin and curries; seasonings such as bean paste, soy sauce, Worceter sauce, ketchup, mayonnaise, dressing, bouillon and roux; processed meat products such as ham, sausage, hamburger, meatball and corned beef, and these products as frozen; frozen processed foods such as pilafs, croquettes, omelets and doria; processed fishery products such as artificial boiled crab paste and boiled fish paste; processed agricultural products such as dried mashed potatoes, jam, marmalade, peanut butter and peanut; others including food boiled down in soy, rice cakes, rice snacks and fast foods; alcoholic beverages such as wines, cocktails, fizzes and liqueur; etc.

However, the dextrin is difficult to use in emulsified foods of the W/O type, such as margarin, since the dextrin incorporated therein is liable to separate off during preservation.

Further when serving as a low calorie bulking agent, the dextrin can be added to the food of the inventionin in an amount which is not limited insofar as the quality of the food is not impaired. However, if adults in good health take the low calorie bulking agent in an amount of 2 g/kg body weight by way of foods of the invention, diarrhea will occur in half of them, so that the amount of the agent to be taken is preferably not greater than half of this value, i.e., up to about 1 g/kg body weight. Nevertheless, since the influence on physiological activities differs from person to person, it is most desirable to alter the amount in view of the effect achieved by the ingestion of the low calorie foods.

To check the indigestible dextrin for characterisitics when it is used in foods, chiefly the product of Example 6 was used in the following experiments to obtain characterisitic dats.

Experimental Example 12

A sensory test was conducted to determine the sweetness of the indigestible dextrin in comparison with that of other saccharides and maltodextrin of DE10, with the sweetness of sucrose taken as 100. Table 30 shows the result.

TABLE 30

| Sample | Sweetness |
| --- | --- |
| Sugar | 100 |
| Glucose | 65 |
| Sorbitol | 50 |
| Maltodextrin (DE25) | 25 |
| Example 6 | 10 |
| Example 7 | 11 |

The indigestible dextrin is about 10 in sweetness, tasting slightly sweet.

Experimental Example 13

Figure 1:
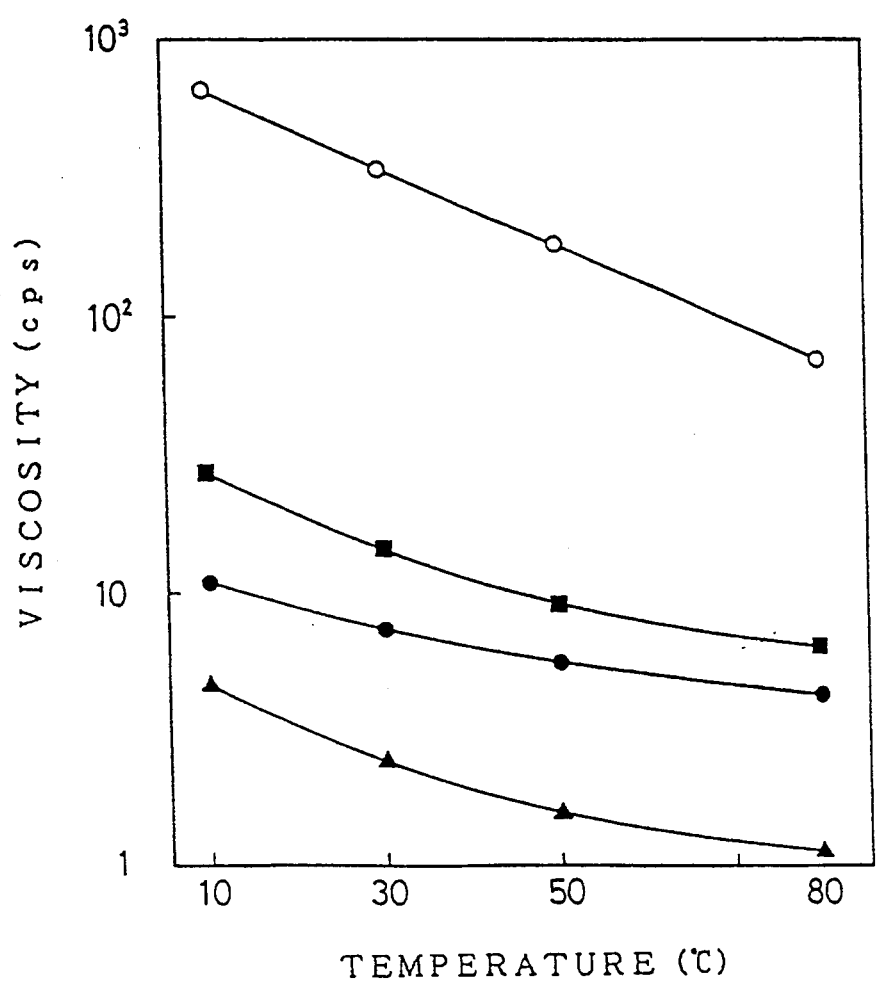
FIG. 1 is a graph showing the relation between the temperature of various substances and the viscosity thereof.

A 30% solution of indigestible dextrin was checked for viscosity at temperatures of 10° to 80° C. using a Brookfield type viscosimeter. FIG. 1 shows the result along with the corresponding values of sucrose, gum arabic and maltodextrin.

The symbols in FIG. 1 stand for the following.
: indigestible dextrin of Example 6
: sucrose
: maltodextrin
○: gum arabic The indigestible dextrin is comparable to maltodextrin in viscosity. This indicates that the indigestible dextrin is usable in foods without entailing a great increase in viscosity.

Experimental Example 14

Coloration Due to Heating in the Presence of Amino Acid

Figure 2:
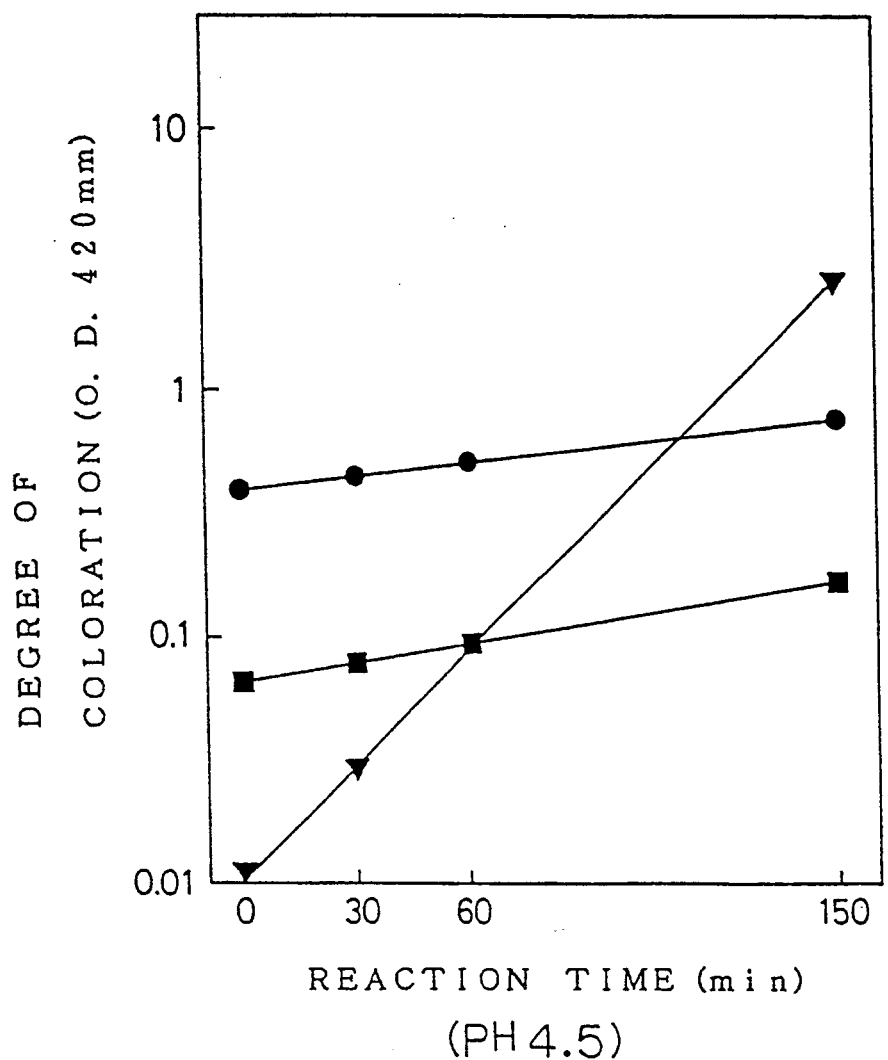
FIG. 2 is a graph showing the relation between the reaction time of various substances and the degree of coloration thereof.
Figure 3:
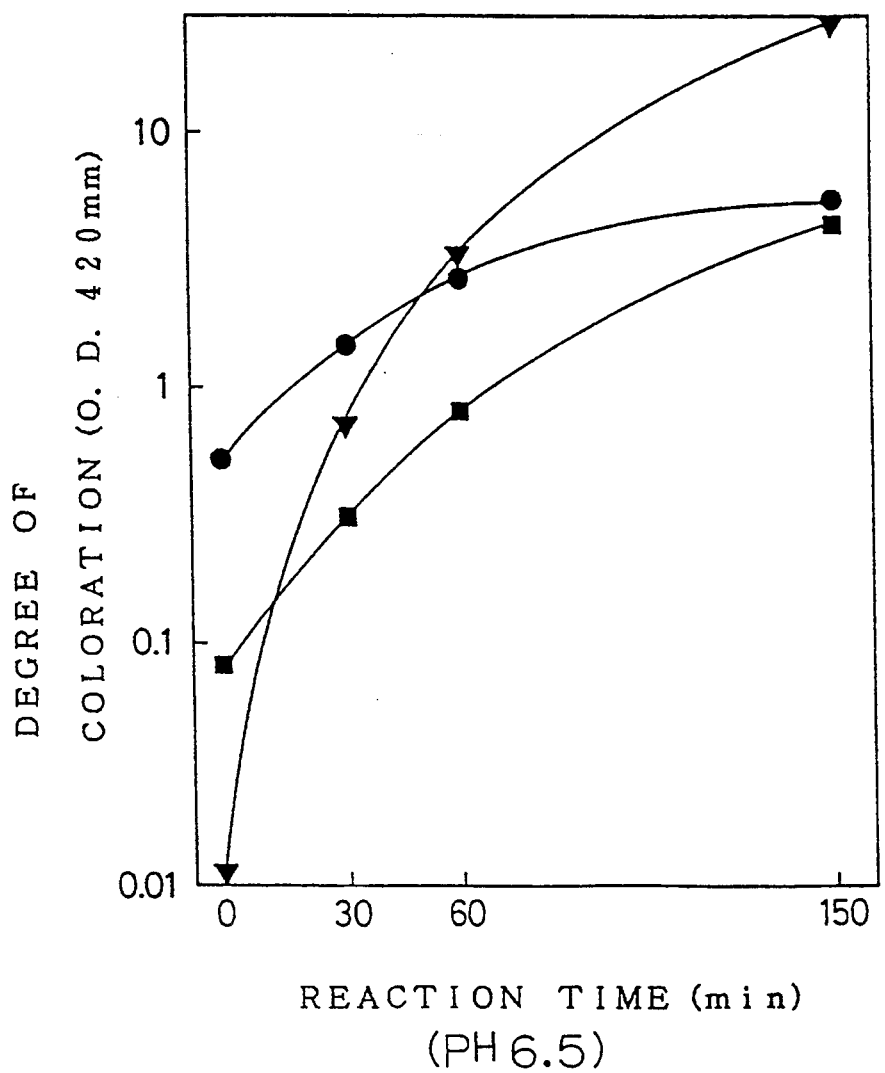
FIG. 3 is a graph showing the relation between the reaction time of various substances and the degree of coloration thereof.

To 10% aqueous solution of indigestible dextrin was added 1% (based on solids) on glycine, and the mixture was heated at 100° C. for 150 minutes and checked for changes in the degree of coloration. The results achieved at pH of 4.5 and pH of 6.5 are shown in FIGS. 2 and 3, respectively. The same smbols as in FIG. 1 were used in these drawings.

The indigestible dextrin is not greatly different in the increase of coloration degree from glucose or maltose. This indicates that the indigestible dextrin is usable generally in the same manner as these materials.

Experimental Example 15

Freezing and Thawing

Figure 4:
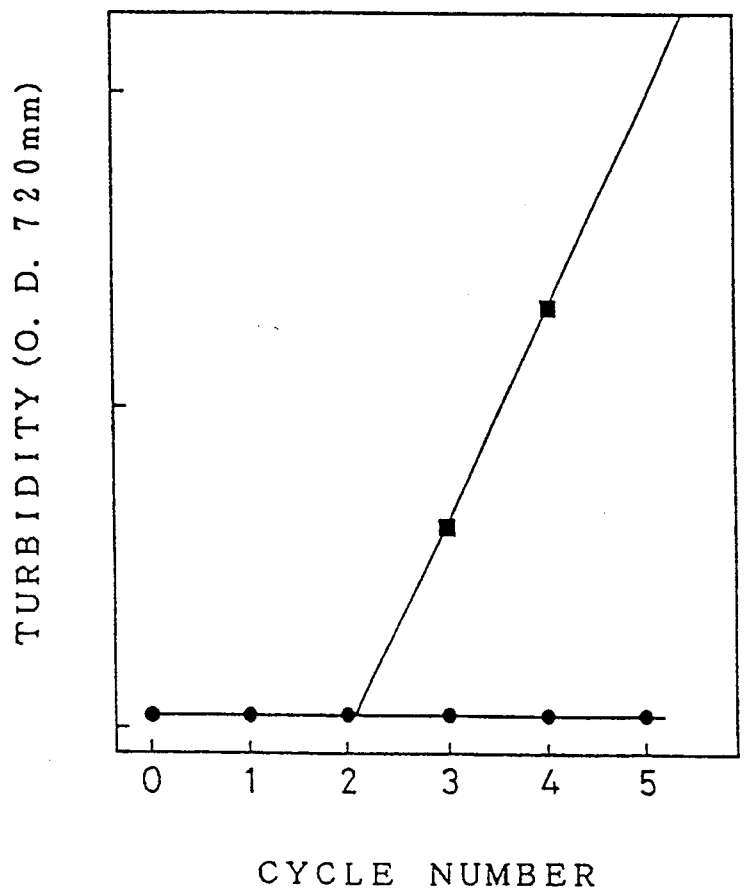
FIG. 4 is a graph showing the relation between the number of freeze-thaw cycles and the turbidity.

A 30% aqueous solution of indigestible dextrin was subjected to five repeated freeze-thaw cycles and then checked for resulting turbidity. FIG. 4 shows the result along with the result achieved by maltodextrin. The symbols used in FIG. 4 have the same meaning as in FIG. 1.

The indigestible dextrin is much less than maltodextrin in increases in turbidity and is therefore very suitable for use in frozen foods.

Experimental Example 16

Freezing Point Depression

Figure 5:
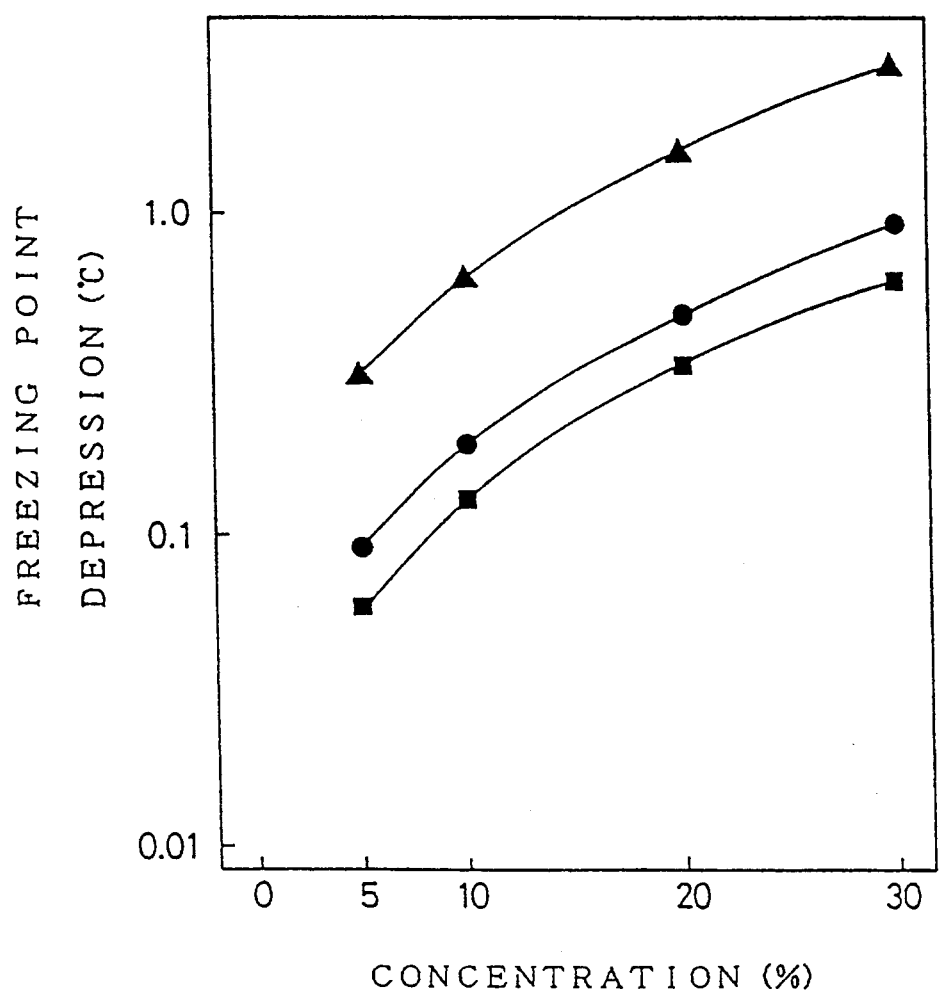
FIG. 5 is a graph showing the relation between the concentration and freezing point depression.

FIG. 5 shows the result obtained by checking 5 to 30% aqueous solutions of indigestible dextrin for freezing point depression along with the result achieved by sucrose and maltodextrin. The symbols in FIG. 5 are the same as in FIG. 1.

The indigestible dextrin is generally intermediate between sugar and maltodextrin in the degree of freezing point depression and is therefore suited to use in ices and the like.

Experimental Example 17

Hygroscopicity

Figure 6:
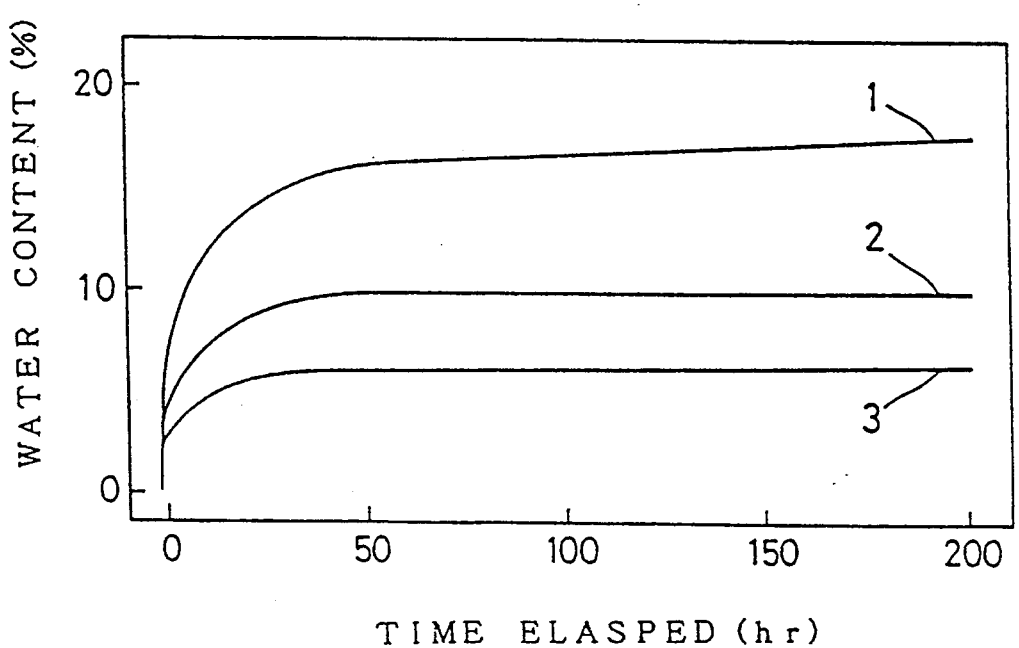
FIG. 6 is a graph showing the relation between the moisture content of indigestible dextrin and the time during which the dextrin is allowed to stand at a predetermined relative humidity.

The indigestible dextrin was made anhydrous by drying and then allowed to stand in a constant-humidity container at 20° C. and a relative humidity of 81%, 52% or 32% for 200 hours. FIG. 6 shows the hygroscopicity of the indigestible dextrin thus determined.

In FIG. 6, the results obtained at R.H. 81%, R.H. 52% and R.H. 32% are indicated at (1), (2) and (3), respectively.

The water content of the indigestible dextrin will not exceed 18% even if preserved for a long period of time. The indigestible dextrin is therefore suited to use in powdery foods.

Experimental Example 18

Mixograph

Figure 7:
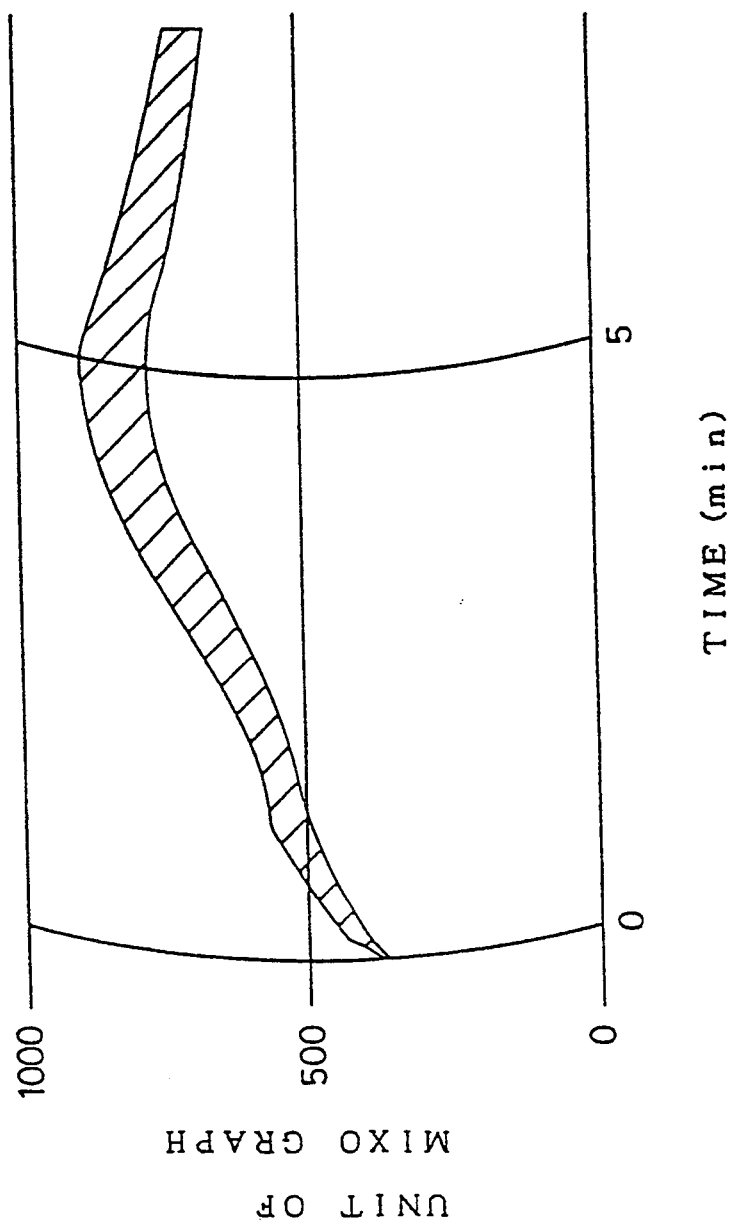
FIG. 7 is a mixograph of a control group.
Figure 9:
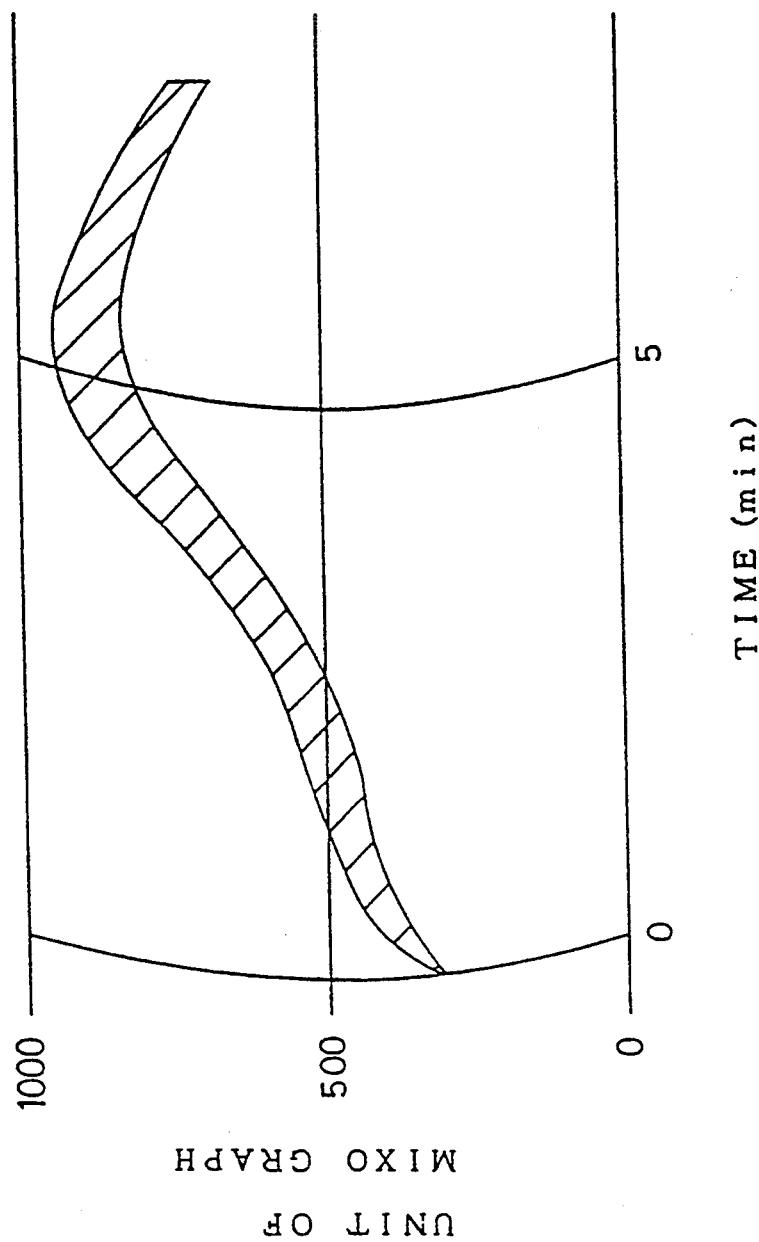
FIG. 9 is a mixograph of indigestible dextrin group of Example 6.

To investigate the behavior of the indigestible dextrin for use in foods having wheat flour incorporated therein, mixograms were prepared using the mixes given in Table 31. FIGS. 7 to 9 show the results. FIG. 7 shows a control mix; FIG. 8, a sugar mix and FIG. 9, an indigestible dextrin mix (low calorie mix containing dietary fiber).

TABLE 31

|  | Control | Sugar | Dietary fiber |
| --- | --- | --- | --- |
| Hard flour (g) | 35.0 | 35.0 | 35.0 |
| Sugar (g) | — | 1.75 | — |
| Example 6 (g) | — | — | 1.75 |
| Water (g) | 26.0 | 25.5 | 25.5 |
| Ratio of water added (%) | 74.3 | 72.9 | 72.9 |
| Developing time (min) | 4.5 | 4.0 | 5.5 |

In the case where the indigestible dextrin was used in place of sucrose, the mix became viscoelastic with a 1.5 minute delay. It was therefore found necessary to lengthen the dough mixing time, to age the dough for a longer period of time or to add the indigestible dextrin during mixing.

Examples of foods embodying the invention will be described next. The indigestible dextrin used will be referred to by the number of example in which it was prepared. The amounts of ingredients and dietary fiber are expressed in grams.

Example 8

Food Example 1

Black tea of the composition given in Table 32 was prepared.

TABLE 32

| Black tea | Control | Example |
|---|---|---|
| Black tea extract | 97.0 | 97.0 |
| Sugar | 3.0 | 3.0 |
| Dextrin (Example 7) | — | 10.0 |
| Dietary fiber | 0 | 2.45 |
| Dietary fiber/240 g | 0 | 5.35 |

Example 9

Food Example 2

Cola of the composition given in Table 33 was prepared.

TABLE 33

| Cola drink | Control | Example |
|---|---|---|
| Sugar | 11.0 | 11.0 |
| Cola base | 0.3 | 0.3 |
| Citric acid | 0.05 | 0.05 |
| Soda water | 88.65 | 88.65 |
| Dextrin (Example 6) | — | 12.0 |
| Dietary fiber | 0 | 5.09 |
| Dietary fiber/240 g | 0 | 10.9 |

Example 10

Food Example 3

Orange juice (30%) was prepared according to the recipe given in Table 34 dissolving powdery ingredients in water, adding concentrated juice and flavoring to the solution and homogenizing the mixture by a homomixer.

TABLE 34

| Orange juice (30%) | Control | Example |
|---|---|---|
| Orange juice concentrate (BX.45) | 6.7 | 6.7 |
| Sugar | 8.1 | 8.1 |
| Citric acid | 0.3 | 0.3 |
| Sodium citrate | 0.1 | 0.1 |
| Orange flavor | 0.3 | 0.3 |
| Water | 84.5 | 84.5 |
| Dextrin (Example 6) | — | 5.0 |
| Dietary fiber | 0.07 | 2.20 |
| Dietary fiber/240 g | 0.17 | 5.03 |

Example 11

Food Example 4

A sports drink was prepared by mixing all ingredients with water according to the recipe of Table 35 and sterilizing the mixture by heating.

TABLE 35

| Sports drink | Control | Example |
|---|---|---|
| Salt | 0.5 | 0.5 |
| Vitamin C | 0.03 | 0.03 |
| Vitamin $B_1$ · Sodium salt | 0.03 | 0.03 |
| Magnesium chloride | 0.2 | 0.2 |
| Calcium lactate | 0.2 | 0.2 |
| Citric acid | 2.4 | 2.4 |
| Sodium citrate | 1.7 | 1.7 |
| Flavor | 2.0 | 2.0 |
| Dextrose | 80.0 | 80.0 |
| Fructose | 12.94 | 12.94 |
| Water | 1500.0 | 1500.0 |
| Dextrin (Example 7) | — | 80.0 |
| Total | 1600.0 | 1680.0 |
| Dietary fiber | 0 | 19.6 |
| Dietary fiber/240 g | 0 | 2.80 |

Example 12

Food example 5

According to the recipe of Table 36, a milk shake was prepared by mixing all ingredients with water, heating the mixture to 80° C. for dissolving, homogenizing the milk fat by a homogenizer, aging the mixture overnight at 5° C., then freezing the mixture, thereafter rapidly cooling the mixture to −40° C. and fully shaking the mixture.

TABLE 36

| Milk shake | Control | Example |
|---|---|---|
| Butter | 5.6 | 1.7 |
| Skimmed milk | 10.5 | 5.5 |
| Dextrin (Example 6) | — | 17.65 |
| Sugar | 9.0 | — |
| Aspartame | — | 0.05 |
| Milk flavor | — | 0.1 |
| Butter flavor | — | 0.1 |
| Sorbitol | 4.0 | 4.0 |
| Emulsifier | 0.7 | 0.7 |
| Water | 70.2 | 70.2 |
| Dietary fiber | 0.1 | 7.57 |
| Dietary fiber/250 g | 0.25 | 18.9 |
| Caloric val.1(K Cal/100 g) | 129 | 80 |
| Caloric val.2(K Cal/100 g) | 129 | 69 |

Example 13

Food Example 6

According to the recipe of Table 37, ice cream was prepared by mixing all ingredients together, heating the mixture to 70° C., stirring the mixture by a homomixer, thereafter homogenizing the mixture by a homogenizer, aging the mixture in a refrigerator for 1 day, freezing the mixture and thereafter rapidly cooling the mixture to −40° C.

TABLE 37

| Ice cream | Control | Example |
|---|---|---|
| Butter | 15.0 | 7.5 |
| Skimmed milk | 10.0 | 5.0 |
| Sugar | 10.0 | — |
| Dextrin (Example 6) | — | 24.27 |
| Emulsifier | 0.7 | 0.7 |
| Milk flavor | — | 0.1 |
| Cream flavor | — | 0.1 |
| Water | 57.3 | 57.3 |
| Aspartame | — | 0.03 |
| Sorbitol | — | 5.0 |
| Maltodextrin (DE 8) | 7.0 | — |
| Dietary fiber | 0.09 | 10.4 |
| Dietary fiber/150 g | 0.14 | 15.6 |
| Caloric val.1(K Cal/100 g) | 216 | 136 |
| Caloric val.2(K Cal/100 g) | 216 | 120 |

Example 14

Food Example 7

According to the recipe of Table 38, fermented skimmed milk was mixed with other ingredients, and the mixture was treated by a homogenizer to prepare a yogurt drink.

TABLE 38

| Yoghurt (Soft) | Control | Example |
|---|---|---|
| Fermented skimmed milk | 40.0 | 40.0 |
| Sugar | 14.0 | 13.0 |
| Stabilizer | 0.35 | 0.35 |
| Flavor | 0.05 | 0.05 |
| Water | 45.6 | 42.6 |
| Dextrin (Example 7) | — | 10.0 |
| Dietary fiber | 0.36 | 2.55 |
| Dietary fiber/240 g | 0.86 | 5.77 |

Example 15

Food Example 8

According to the recipe of Table 39, hard yoghurt was prepared by adding a hardening agent to skimmed milk, innoculating the mixture with 3% of starter, refrigerating the mixture when acidity of 0.7% was attained, mixing the mixture with other ingredients by stirring and refrigerating the resulting mixture again.

TABLE 39

| Yoghurt (Hard) | Control | Example |
|---|---|---|
| Skimmed milk | 90.9 | 90.9 |
| Sugar | 9.1 | — |
| Dextrin (Example 6) | — | 9.1 |
| Stevioside | — | 0.05 |
| Flavor | Small amt. | Small amt. |
| Gelatin | Small amt. | Small amt. |
| Dietary fiber | 0.07 | 3.93 |
| Dietary fiber/150 g | 0.1 | 5.90 |
| Caloric val.1(K Cal/100 g) | 64 | 45 |
| Caloric val.2(K Cal/100 g) | 64 | 39 |

Example 16

Food Example 9

According to the recipe of Table 40, a powder of coffee whitener was prepared by dissolving water-soluble ingredients in 66.6% of hot water based on the dry weight of the ingredients, dissolving an emulsifying agent in oil, mixing together and homogenizing the two solutions at 60° C. to obtain an emulsion, and thereafter spray-drying the emulsion.

TABLE 40

| Coffee whitener | Control | Example |
|---|---|---|
| Hardened soy bean oil | 50.0 | 50.0 |
| Corn syrup solid (DE 40) | 49.0 | — |
| Emulsifier | 0.84 | 0.84 |
| Cream flavor | 0.16 | 0.16 |
| Dextrin (Example 6) | — | 49.0 |
| Dietary fiber | 0 | 20.8 |
| Dietary fiber/12 g | 0 | 2.49 |
| Caloric val.1(K Cal/100 g) | 647 | 555 |
| Caloric val.2(K Cal/100 g) | 647 | 523 |

Example 17

Food Example 10

Candy was prepared by dissolving the ingredients of Table 41 other than the flavor in water, concentrating the solution to Bx 80°, boiling down the concentrate by an evaporator, cooling the resulting concentrate to 40° C., admixing the flavor therewith and molding the mixture.

TABLE 41

| Candy | Control | Example |
|---|---|---|
| Corn syrup | 49.4 | 24.7 |
| Citric acid | 0.5 | 0.5 |
| Flavor | 0.1 | 0.1 |
| Sugar | 50.0 | 20.0 |
| Dextrin (Example 7) | — | 54.6 |
| Stevioside | — | 0.1 |
| Dietary fiber | 0 | 13.4 |
| Dietary fiber/12 g | 0 | 1.61 |
| Caloric val.1(K Cal/100 g) | 359 | 275 |
| Caloric val.2(K Cal/100 g) | 359 | 248 |

Example 18

Food Example 11

The ingredients of Table 42 other than the carbohydrates and flavor were placed into a pan, heated for melting and thoroughly mixed together. Chewing gum was prepared by admixing the carbohydrates with the mixture as cooled to 50° C., followed by addition of the flavor at 40° C., molding and standing for cooling.

TABLE 42

| Chewing gum | Control | Example |
|---|---|---|
| Poly-Vinylacetate | 20.0 | 20.0 |
| Plasticizer | 3.0 | 3.0 |
| Poly-isobutyrene | 3.0 | 3.0 |
| Micro-crystalline wax | 2.0 | 2.0 |
| Calcium carbonate | 2.0 | 2.0 |
| Sugar (powder) | 45.0 | — |
| Dextrose | 24.0 | — |
| Dextrin (Example 7) | — | 68.7 |
| Aspartame | — | 0.3 |
| Flavor | 1.0 | 1.0 |
| Dietary fiber | 0 | 16.8 |
| Dietary fiber/32 g | 0 | 5.39 |
| Caloric val.1(K Cal/100 g) | 270 | 150 |
| Caloric val.2(K Cal/100 g) | 270 | 117 |

Example 19

Food Example 12

All ingredients of Table 43 were thoroughly mixed together at 40° C. and further kneaded in an attritor for a long period of time to pulverize the particles, followed by molding and cooling to prepare a sweet chocolate.

TABLE 43

| Sweet chocolate | Control | Example |
|---|---|---|
| Bitter chocolate | 33.2 | 33.2 |
| Sugar | 55.4 | — |
| Dextrin (Example 6) | — | 54.4 |
| Aspartame | — | 0.31 |
| cacao butter | 11.1 | 11.1 |
| Dietary fiber | 0.0 | 23.1 |
| Dietary fiber/100 g | 0.0 | 23.1 |
| Caloric val.1 (KCal/100 g) | 450 | 345 |
| Caloric val.2 (KCal/100 g) | 450 | 309 |

Example 20

Food Example 13

According to the recipe of Table 44, wheat flour, modified starch and egg yolk (powder) were admixed with a small amount of water. A solution of the other materials as dissolved in the remaining portion of water at 80° C. was added to the mixture while using a whip, and the resulting mixture was boiled on an intense fire to prepare custard cream.

TABLE 44

| Custard cream | Control | Example |
|---|---|---|
| Sugar | 13.5 | — |
| Dextrose | 9.0 | — |
| Corn syrup (DE 40) | 12.3 | 6.2 |
| Water | 41.0 | 41.9 |
| Dextrin (Example 7) | — | 31.59 |
| Stevioside | — | 0.11 |
| Wheat flour | 3.8 | 3.8 |
| Modified starch | 7.0 | 7.0 |
| Skimmed milk | 1.3 | 1.3 |
| Margarine | 11.9 | 7.9 |
| Egg yolk powder | 0.2 | 0.2 |
| Dietary fiber | 0.092 | 7.83 |
| Dietary fiber/50 g | 0.092 | 3.92 |
| Caloric val.1 (KCal/100 g) | 258 | 190 |
| Caloric val.1 (KCal/100 g) | 258 | 174 |

Example 21

Food Example 14

According to the recipe of Table 45, gelatine was dissolved in 25 g of water, and all the other ingredients except aspartame were dissolved in the remaining portion of water. The solutions were cooled to 40° C., then all the ingredients were mixed together, and the resulting mixture was refrigerated to prepare an orange jelly.

TABLE 45

| Orange gelly | Control | Example |
|---|---|---|
| Sugar | 20.8 | — |
| Dextrin (Example 6) | — | 20.8 |
| Aspartame | — | 0.11 |
| Water | 34.7 | 34.7 |
| Gelatine | 2.8 | 2.8 |
| Orange juice | 31.2 | 31.2 |
| Curacao | 10.4 | 10.4 |
| Dietary fiber | 0.09 | 8.91 |
| Dietary fiber/100 g | 0.09 | 8.91 |
| Caloric val.1 (KCal/100 g) | 131 | 92 |
| Caloric val.2 (KCal/100 g) | 131 | 79 |

Example 22

Food Example 15

According to the recipe of Table 46, the ingredients other than pectin were mixed together, lightly pulverized by a mixer and then heated on a low fire. Upon evaporation of 20% of the water, pectin was added to the mixture, followed by cooling to prepare strawberry jam.

TABLE 46

| Strawberry jam | Control | Example |
|---|---|---|
| Flesh strawberry | 55.0 | 55.0 |
| Sugar | 45.0 | — |
| Dextrin (Example 6) | — | 45.0 |
| Pectin | 0.1 | 0.1 |
| Citric acid | 0.1 | 0.1 |
| Aspartame | — | 0.25 |
| Dietary fiber | 0.93 | 20.0 |
| Dietary fiber/10 g | 0.093 | 2.00 |
| Caloric val.1 (KCal/100 g) | 266 | 136 |
| Caloric val.2 (KCal/100 g) | 266 | 95 |

Example 23

Food Example 16

According to the recipe of Table 47, granulated sugar, water and indigestible dextrin were added to pared apples, and the mixture was boiled on a medium fire. When the apples became semi-transparent, lemon juice was added to the mixture, followed by boiling down on a medium fire without scorching. When the apples became soft, the mixture was strained and further boiled down to Bx 70° to prepare apple jam.

TABLE 47

| Apple jam | Control | Example |
|---|---|---|
| Flesh apple | 55.4 | 55.4 |
| Sugar | 24.0 | 24.0 |
| Lemon juice | 2.2 | 2.2 |
| Water | 18.4 | 18.4 |
| Dextrin (Example 6) | — | 10.0 |
| Dietary fiber | 0.88 | 5.12 |
| Dietary fiber/30 g | 0.58 | 2.56 |

Example 24

Food Example 17

According to the recipe of Table 48, the whole amount of indigestible dextrin and stevioside were added to 30 g of water to prepare a syrup, which was then heated. When the syrup became boiled up, bean paste was added thereto. The mixture was boiled down to an amount weighing 100 g to prepare bean jam.

TABLE 48

| Bean jam | Control | Example |
|---|---|---|
| Bean paste | 59.0 | 59.0 |
| Sugar | 41.0 | — |
| Dextrin (Example 7) | — | 40.77 |
| Stevioside | — | 0.23 |
| Dietary fiber | 4.25 | 14.2 |
| Dietary figer/100 g | 4.25 | 14.2 |
| Caloric val.1 (KCal/100 g) | 249 | 186 |
| Caloric val.2 (KCal/100 g) | 249 | 166 |

Example 25

Food Example 18

According to the recipe given in Table 49, 23.6 g of water, indigestible dextrin and stevioside were added to agar-agar swollen with water, and the mixture was heated for boiling and dissolving, strained and then boiled again, followed by addition of bean paste. The mixture was boiled down to an amount weighing 100 g, then moled and cooled to prepare a sweet jelly of beans.

TABLE 49

| Sweet jelly of beans | Control | Example |
|---|---|---|
| Bean paste | 36.8 | 36.8 |
| Agar-agar | 0.8 | 0.8 |
| Water | 7.2 | 7.2 |
| Sugar | 55.2 | — |
| Dextrin (Example 7) | — | 54.9 |
| Stevioside | — | 0.3 |
| Dietary fiber | 2.65 | 16.1 |
| Dietary fiber/40 g | 1.06 | 6.44 |
| Caloric val.1 (KCal/100 g) | 269 | 170 |
| Caloric val.2 (KCal/100 g) | 269 | 143 |

Example 26

Food Example 19

A cereal was dipped in a solution of indigestible dextrin, Bx 50°, according to the recipe of Table 50 and dried overnight at 40° C. to prepare a processed cereal. The product was glossier than a control, and the original water retentivity of 2.7% increased to 7.0%.

TABLE 50

| Cereal | Control | Example |
| --- | --- | --- |
| Cereal | 100.0 | 53.8 |
| Dextrin (Example 6) | — | 42.6 |
| Dietary fiber | 2.90 | 19.6 |
| Dietary fiber/40 g | 1.16 | 7.85 |
| Caloric val.1 (KCal/100 g) | 389 | 286 |
| Caloric val.2 (KCal/100 g) | 389 | 257 |

Example 27

Food Example 20

According to the recipe given in Table 51, indigestible dextrin was uniformly kneaded with wheat flour and further kneaded therewith while adding water in small portions to prepare spaghetti.

TABLE 51

| Spaghetti | Control | Example |
| --- | --- | --- |
| Wheat flour | 100.0 | 100.0 |
| Water | 30.0 | 25.0 |
| Dextrin (Example 6) | — | 5.0 |
| Dietary fiber | 2.10 | 4.18 |
| Dietary fiber/200 g | 3.23 | 6.43 |

Example 28

Food Example 21

The ingredients of Table 52 were fully kneaded together to obtain dough, which was then fermented and baked to prepare loaves of bread.

TABLE 52

| White bread | Control | Example |
| --- | --- | --- |
| Wheat flour | 100.0 | 100.0 |
| Water | 61.0 | 61.0 |
| Baker's yeast | 3.0 | 3.0 |
| Salt | 2.0 | 2.0 |
| Sugar | 6.0 | 6.0 |
| Skimmed milk | 3.0 | 3.0 |
| Shortening | 5.0 | 5.0 |
| Extrin (Example 6) | — | 5.0 |
| Dietary fiber/180 g | 2.13 | 4.21 |

Example 29

Food Example 22

According to the recipe of Table 53, milk and eggs were added to wheat flour, and the other ingredients were added to the mixture with kneading to obtain uniform dough, which was then molded and fried in oil at 160° to 180° C. while turning the molded pieces upside down. The fried pieces were drained the oil to obtain American doughnut.

TABLE 53

| American doughnut | Control | Example |
| --- | --- | --- |
| Wheat flour | 100.0 | 100.0 |
| Sugar | 29.2 | 29.2 |
| Egg (Whole) | 22.2 | 22.2 |

TABLE 53-continued

| American doughnut | Control | Example |
| --- | --- | --- |
| Milk | 40.2 | 40.2 |
| Butter | 5.0 | 5.0 |
| Salt | 0.2 | 0.2 |
| Lemon flavor | 0.2 | 0.2 |
| Baking powder | 3.0 | 3.0 |
| Dextrin (Example 7) | — | 20.0 |
| Dietary fiber | 2.20 | 7.10 |
| Dietary fiber/100 g | 1.10 | 3.23 |

Example 30

Food Example 23

According to the recipe of Table 54, egg white and water were fully mixed together to obtain a whipped mixture, to which indigestible dextrin, Avicel and hard wheat flour were successively added with kneading to prepare a uniform mixture. The mixture was freeze-dried to avoid thermal denaturation of the egg white and prepare a replacer for wheat flour.

TABLE 54

| Wheat flour replacer | Control | Example |
| --- | --- | --- |
| Soft wheat flour | 100.0 | — |
| Dextrin (Example 6) | — | 40.0 |
| Egg white | — | 10.0 |
| Water | — | 10.0 |
| Avicel | — | 25.0 |
| Hard wheat flour | — | 15.0 |
| Dietary fiber | 2.10 | 42.4 |
| Caloric val.1 (KCal/100 g) | 368 | 163 |
| Caloric val.2 (KCal/100 g) | 386 | 137 |

Example 31

Food Example 24

All ingredients listed in Table 55 and including the flour replacer of food example 23 were kneaded together. The mixture, when becoming elastic, was spread out flat and blanked out. The resulting pieces were baked at 190° C. for 10 minutes, affording butter cookies.

TABLE 55

| Butter cookie | Control | Example |
| --- | --- | --- |
| Wheat flour | 47.6 | — |
| Wheat flour replacer | — | 47.6 |
| Sugar | 19.1 | — |
| Dextrin (Example 6) | — | 27.0 |
| Stevioside | — | 0.1 |
| Shortening | 21.4 | 13.4 |
| Water | 11.9 | 11.9 |
| Dietary fiber | 1.00 | 31.4 |
| Dietary fiber/30 g | 0.30 | 9.42 |
| Caloric val.1 (KCal/100 g) | 446 | 249 |
| Caloric val.2 (KCal/100 g) | 446 | 219 |

Example 32

Food Example 25

According to the recipe of Table 56, all ingredients including the flour replacer of food example 23 were mixed with water and treated with a whip for stirring and dissolving to obtain uniform dough, which was then baked at 180° C. for 50 minutes to prepare a pound cake.

TABLE 56

| Pound cake | Control | Example |
|---|---|---|
| Wheat flour | 23.0 | — |
| Wheat flour replacer | — | 23.0 |
| Sugar | 28.8 | — |
| Dextrin (Example 7) | — | 37.3 |
| Stevioside | — | 0.1 |
| Egg (whole) | 17.2 | 17.2 |
| Milk | 6.9 | 6.9 |
| Shortening | 17.2 | 8.6 |
| Water | 6.9 | 6.9 |
| Dietary fiber | 0.51 | 18.9 |
| Dietary fiber/100 g | 0.51 | 18.9 |
| Caloric val.1 (KCal/100 g) | 386 | 220 |
| Caloric val.2 (KCal/100 g) | 386 | 208 |

Example 33

Food Example 26

According to the recipe of Table 57, all ingredients including the flour replacer of food example 23 were mixed with water, and the mixture was stirred with a whip to incorporate air bubbles into the mixture. The mixture was baked at 180° C. for 40 minutes to prepare a sponge cake.

TABLE 57

| Sponge cake | Control | Example |
|---|---|---|
| Wheat flour | 33.3 | — |
| Wheat flour replacer | — | 33.3 |
| Sugar | 33.4 | — |
| Egg (whole) | 33.3 | 33.3 |
| Dextrin (Example 7) | — | 33.3 |
| Stevioside | — | 0.1 |
| Dietary fiber | 0.73 | 22.3 |
| Dietary fiber/100 g | 0.73 | 22.3 |
| Caloric val.1 (KCal/100 g) | 305 | 177 |
| Caloric val.2 (KCal/100 g) | 305 | 152 |

Example 34

Food Example 27

According to the recipe of Table 58, crust dough was prepared by full kneading and repeated folding. The inner ingredient was boiled down until it became half-deformed. The dough and inner ingredient were molded and then baked to prepare an apple pie.

TABLE 58

| Apple pie | Control | Example |
|---|---|---|
| Soft wheat flour | 100.0 | 100.0 |
| Hard wheat flour | 100.0 | 100.0 |
| Butter | 180.0 | 180.0 |
| Water | 105.0 | 105.0 |
| Apple | 300.0 | 300.0 |
| Sugar | 90.0 | 90.0 |
| Cinnamon powder | 1.0 | 1.0 |
| Egg yolk | 10.0 | 10.0 |
| Dextrin (Example 6) | — | 40.0 |
| Dietary fiber | 9.01 | 25.6 |
| Dietary fiber (1/6) | 1.50 | 4.27 |

Example 35

Food Example 28

According to the recipe of Table 59, corn cream soup was prepared by boiling corn in water until no unboiled portion remained, then adding the other ingredients and boiling down the mixture.

TABLE 59

| Corn cream soup | Control | Example |
|---|---|---|
| Milk | 19.8 | 19.8 |
| Sweet corn | 18.4 | 18.4 |
| Butter | 2.3 | 2.3 |
| Wheat flour | 2.0 | 2.0 |
| Salt | 1.0 | 1.0 |
| Seasonings | 0.2 | 0.2 |
| Spices | 0.2 | 0.2 |
| Water | 56.1 | 56.1 |
| Dextrin (Example 7) | — | 6.0 |
| Dietary fiber | 0.45 | 1.92 |
| Dietary fiber/200 g | 0.90 | 3.62 |

Example 36

Food Example 29

According to the recipe given in Table 60, sparerib was pan-fried and placed into another pan. Vegetables were also pan-fried and transferred onto the pan. Wheat flour and curry powder were pan-fried into a brown roux. All the ingredients were boiled down in the pan to prepare a retorted curry.

TABLE 60

| Retorted pauch curry | Control | Example |
|---|---|---|
| Spare rib | 12.4 | 12.4 |
| Salt | 0.5 | 0.5 |
| Butter | 6.2 | 5.2 |
| Water | 49.0 | 49.0 |
| Potato | 12.4 | 8.4 |
| Onion | 12.4 | 12.4 |
| Carrot | 2.5 | 2.5 |
| Wheat flour | 3.6 | 3.6 |
| Curry powder | 0.5 | 0.5 |
| Spices | 0.5 | 0.5 |
| Dextrin (Example 6) | — | 5.0 |
| Dietary fiber | 0.57 | 2.65 |
| Dietary fiber/200 g | 1.14 | 5.05 |

Example 37

Food Example 30

According to the recipe of Table 61, meat was fully pan-fried and then placed into another pan. Vegetables, especially onions, were fully pan-fried. All the ingredients were then boiled down in the pan for 3 hours to prepare beef stew.

TABLE 61

| Beef stew | Control | Example |
|---|---|---|
| Spare rib | 15.5 | 15.5 |
| Salt | 0.2 | 0.2 |
| Wheat flour | 2.7 | 2.7 |
| Salad oil | 3.9 | 3.9 |
| Onion | 9.7 | 9.7 |
| Potato | 13.6 | 13.6 |
| Carrot | 5.8 | 5.8 |
| Green beans | 1.9 | 1.9 |
| Seasoning (liquid) | 38.8 | 38.8 |
| Butter | 1.9 | 1.9 |
| Tomato puree | 5.8 | 5.8 |
| White pepper | 0.2 | 0.2 |
| Dextrin (Example 6) | — | 5.0 |
| Dietary fiber | 0.78 | 2.86 |
| Dietary fiber/300 g | 2.34 | 8.17 |

Example 38

Food Example 31

Non-oil dressing was prepared according to the recipe of Table 62 by mixing liquid ingredients together and thereafter dissolving powdery ingredients in the mixture.

TABLE 62

| Non-oil dressing | Control | Example |
|---|---|---|
| Vinegar | 30.8 | 30.8 |
| Sugar | 4.0 | 4.0 |
| Salt | 0.5 | 0.5 |
| Soy-sauce | 8.4 | 8.4 |
| Seasoning (liquid) | 26.3 | 26.3 |
| Corn sirup solid | 30.0 | — |
| Dextrin (Example 6) | — | 30.0 |
| Dietary fiber | 0 | 12.5 |
| Dietary fiber/20 g | 0 | 2.49 |
| Caloric val.1 (KCal/100 g) | 163 | 102 |
| Caloric val.2 (KCal/100 g) | 163 | 83 |

Example 39

Food Example 32

According to the recipe of Table 63, powdery ingredients other than Xanthan gum were dissolved in water, and the solution was heated to 80° C. Upon the solution reaching 40° C., vinegar was added, and the mixture was treated by a homomixer driven at a medium speed while adding salad oil in small portions to the mixture to obtain an emulsion. Xanthan gum was dissolved in the emulsion with the homomixer driver at a low speed to prepare dressing of the emulsion type.

TABLE 63

| Dressing | Control | Example |
|---|---|---|
| Salad oil | 30.0 | 15.0 |
| Emulstar #30 | 3.0 | 3.0 |
| Xanthan gum | 0.2 | 0.2 |
| Vinegar | 15.0 | 15.0 |
| Salt | 1.3 | 1.3 |
| Sugar | 2.7 | 2.7 |
| Dextrin (Example 7) | — | 10.5 |
| Water | 47.8 | 52.3 |
| Dietary fiber | 0.2 | 2.78 |
| Dietary fiber/20 g | 0.04 | 0.56 |
| Caloric val.1 (KCal/100 g) | 301 | 196 |
| Caloric val.2 (KCal/100 g) | 301 | 192 |

"Emulster #30" listed in Table 63 is a tradename of lipophilic modified starch (product of Matsutani Chemical Industry Co., Ltd.).

Example 40

Food Example 33

According to the recipe of Table 64, powdery ingredients were dissolved in water and vinegar, and egg yolk was admixed with the solution. The mixture was treated by a homomixer driven at a medium speed while adding salad oil thereto in small portions for emulsification to prepare mayonnaise.

TABLE 64

| Mayonnaise | Control | Example |
|---|---|---|
| Salad oil | 70.0 | 35.0 |
| Vinegar | 10.0 | 10.0 |
| Egg yolk | 17.5 | 10.0 |
| Salt | 1.5 | 1.5 |
| Sugar | 1.0 | 1.0 |
| Dextrin (Example 6) | — | 25.0 |
| Water | — | 17.5 |
| Dietary fiber | 0.02 | 10.4 |
| Dietary fiber/20 g | 0.004 | 2.08 |
| Caloric val.1 (KCal/100 g) | 714 | 409 |
| Caloric val.2 (KCal/100 g) | 714 | 393 |

Example 41

Food Example 43

Peanut butter was prepared according to the recipe of Table 65 by crushing raw peanut, pulverizing the peanut with an attritor and admixing other ingredients therewith.

TABLE 65

| Peanut Butter | Control | Example |
|---|---|---|
| Peanut | 50.0 | 33.0 |
| Palm oil | 50.0 | 33.0 |
| Dextrin (Example 6) | — | 33.9 |
| Peanut flavor | — | 0.1 |
| Dietary fiber | 4.35 | 17.0 |
| Dietary fiber/20 g | 0.87 | 3.39 |
| Caloric val. 1 (KCal/100 g) | 741 | 549 |
| Caloric val. 2 (KCal/100 g) | 741 | 527 |

Example 42

Food Example 53

The powdery ingredients listed in the recipe Table 66 were uniformly mixed together to prepare cheese powder.

TABLE 66

| Cheese powder | Control | Example |
|---|---|---|
| Cheese powder | 100.0 | 50.0 |
| Dextrin (Example 7) | — | 49.9 |
| Dietary fiber | 0.60 | 12.5 |
| Dietary fiber/10 g | 0.06 | 1.25 |
| Caloric val. 1 (KCal/100 g) | 562 | 385 |
| Caloric val. 2 (KCal/100 g) | 562 | 360 |

Example 43

Food Example 36

According to the recipe of Table 67, lactobacillus starter and rennet were added to a mixture of fresh cream and indigestible dextrin, followed by standing at 20° C. for 15 hours. With addition of a flavor, the mixture was kneaded in an attritor and then cooled to prepare cream cheese.

TABLE 67

| Cream cheese | Control | Example |
|---|---|---|
| Flesh cream | 100.0 | 50.0 |
| Dextrin (Example 6) | — | 35.0 |
| Water | — | 14.8 |
| Cheese oil | — | 0.1 |
| Cream flavor | — | 0.1 |
| Dietary fiber | 0.0 | 14.6 |
| Dietary fiber/20 g | 0.0 | 2.91 |
| Caloric val. 1 (KCal/100 g) | 431 | 280 |
| Caloric val. 2 (KCal/100 g) | 431 | 257 |

Example 44

Food Example 37

White sauce was prepared according to the recipe of Table 68 by pan-frying soft wheat flour in butter, then mixing other ingredients therewith and boiling down the mixture until the mixture became thickened.

TABLE 68

| White sauce | Control | Example |
|---|---|---|
| Butter | 8.0 | 4.0 |
| Dextrin (Example 7) | — | 4.0 |
| Water | — | 35.9 |

TABLE 68-continued

| White sauce | Control | Example |
|---|---|---|
| Soft wheat flour | 9.0 | — |
| Hard wheat flour | — | 7.0 |
| Milk | 68.0 | 34.0 |
| Milk flavor | — | 0.1 |
| Seasoning (liquid) | 13.9 | 13.9 |
| Salt | 1.0 | 1.0 |
| White pepper | 0.1 | 0.1 |
| Dietary fiber | 0.33 | 1.20 |
| Caloric val. 1 (KCal/100 g) | 134 | 85 |
| Caloric val. 2 (KCal/100 g) | 134 | 83 |

Example 45

Food Example 38

Meat sauce was prepared according to the recipe of Table 69 by pan-frying minced pork, onions and carrots in fat, pan-frying these ingredients again with addition of wheat flour, admixing other ingredients with the mixture and boiling down the resulting mixture until the mixture became thickened.

TABLE 69

| Meat sauce | Control | Example |
|---|---|---|
| Poke (minced) | 8.2 | 8.2 |
| Fat (cow) | 5.0 | — |
| Dextrin (Example 6) | — | 5.0 |
| Water | 16.0 | 18.5 |
| Onion | 30.0 | 30.0 |
| Carrot | 6.0 | 6.0 |
| Tomato ketchap | 8.5 | 8.5 |
| Tomato puree | 8.5 | 8.5 |
| Apple (boiled) | 12.5 | 12.5 |
| Sugar | 1.7 | 1.7 |
| Salt | 0.8 | 0.8 |
| Spices and seasonings | 1.8 | 1.8 |
| Wheat flour | 1.0 | 1.0 |
| Dietary fiber | 0.98 | 3.06 |
| Dietary fiber/100 g | 0.98 | 3.06 |
| Caloric val. 1 (KCal/100 g) | 105 | 77 |
| Caloric val. 2 (KCal/100 g) | 105 | 73 |

Example 46

Food Example 39

Sausage of beef and pork was prepared according to the recipe of Table 70 by crushing raw ingredients to prepare a mixture, filling the mixture into a film bag, allowing the mixture to stand as salt-pickled at 5° C. for 12 hours and thereafter boiling the mixture at 75° C. for 90 minutes, followed by refrigeration.

TABLE 70

| Beef and poke sausage | Control | Example |
|---|---|---|
| Beef | 22.0 | 22.0 |
| Ice | 17.29 | 17.29 |
| Salt | 1.7 | 1.7 |
| Pickles | 0.01 | 0.01 |
| Sugar | 1.0 | 1.0 |
| Sodium glutamate | 0.5 | 0.5 |
| Spices | 0.5 | 0.5 |
| Potato starch | 3.0 | 3.0 |
| Poke (shoulder) | 54.0 | 54.0 |
| Dextrin (Example 6) | — | 10.0 |
| Dietary fiber | 0.20 | 4.36 |
| Dietary fiber/100 g | 0.20 | 3.96 |

Example 47

Food Example 40

Corned beef was prepared from beef as held in a salt pickling solution for 5 days and boiled at 115° C. for 90 minutes for the removal of water and fat. According to the recipe shown in Table 71, the other material was admixed with the beef to prepare a uniform mixture, which was then filled into a film bag, sterilized at 75° C. for 60 minutes and thereafter refrigerated.

TABLE 71

| Corned beef | Control | Example |
|---|---|---|
| Beef (pickled and boiled) | 80.0 | 80.0 |
| Fat (cow) | 20.0 | 5.0 |
| Dextrin (Example 6) | — | 10.0 |
| Water | — | 5.0 |
| Dietary fiber | 0.48 | 4.64 |
| Dietary fiber/50 g | 0.24 | 2.32 |
| Caloric val. 1 (KCal/100 g) | 245 | 154 |
| Caloric val. 2 (KCal/100 g) | 245 | 147 |

Example 48

Food Example 41

According to the recipe of Table 72, onions and beef were minced and mixed with all the other ingredients, and the mixture was uniformly kneaded and molded. The molded piece was griddled on iron plate at 180° C. over each side for 30 seconds, then boiled at 100° C. for 10 minutes, cooled and thereafter frozen to obtain a frozen hamburger.

TABLE 72

| Hamburg steak | Control | Example |
|---|---|---|
| Processed meat (minced) | 38.8 | 38.8 |
| Fat (cow) | 20.0 | 5.0 |
| Dextrin (Example 7) | — | 14.0 |
| Water | — | 5.0 |
| Onion | 20.0 | 20.0 |
| Fresh crumb | 10.0 | 8.0 |
| Starch | 10.0 | 8.0 |
| Seasonings and spices | 1.2 | 1.2 |
| Dietary fiber | 0.59 | 4.02 |
| Dietary fiber/200 g | 1.18 | 8.04 |
| Caloric val. 1 (KCal/100 g) | 336 | 238 |
| Caloric val. 2 (KCal/100 g) | 336 | 232 |

Example 49

Food Example 42

Hamburger putty was prepared according to the recipe of Table 73 by crushing the ingredients into a mixture, filling the mixture into a film bag having a diameter of 8 cm, thereafter freezing the mixture at −30° C. and cutting the mixture into slices, 8 mm in thickness, by a slicer.

TABLE 73

| Hamburger putty | Control | Example |
|---|---|---|
| Beef | 50.0 | 50.0 |
| Poke | 25.0 | 25.0 |
| Fat (cow) | 10.0 | 10.0 |
| Onion | 10.0 | 10.0 |
| Spices | 0.5 | 0.5 |
| Salt | 1.0 | 1.0 |
| Sugar | 1.0 | 1.0 |
| Egg (whole) | 2.5 | 2.5 |
| Dextrin (Example 6) | — | 10.0 |
| Dietary fiber | 0.48 | 4.64 |
| Dietary fiber/60 g | 0.29 | 2.53 |

Example 50

Food Example 43

Liver paste was prepared according to the recipe of Table 74 by boiling liver, beef and belly at 100° C. for 5 seconds, then crushing these ingredients, mixing them with the other ingredients, boiling the mixture at 80° C. with full stirring and refrigerating the mixture.

TABLE 74

| Liver paste | Control | Example |
|---|---|---|
| Liver | 30.0 | 30.0 |
| Beef | 12.0 | 12.0 |
| Beef (belly) | 25.69 | 16.5 |
| Lard | 20.0 | 5.0 |
| Dextrin (Example 6) | — | 19.19 |
| Water | | 5.0 |
| Soup | 8.0 | 8.0 |
| Spices | 2.3 | 2.3 |
| Salt | 2.0 | 2.0 |
| Sodium nitrite | 0.01 | 0.01 |
| Dietary fiber | 0.41 | 8.39 |
| Dietary fiber/30 g | 0.12 | 2.52 |
| Caloric val. 1 (KCal/100 g) | 330 | 213 |
| Caloric val. 2 (KCal/100 g) | 330 | 200 |

Example 51

Food Example 44

The dough ingredients listed in Table 75 were fully kneaded together, then fermented at 40° C. for 30 minutes in a heat-insulated device and cut into pieces of suitable size, which were spread out with a needle rod. The ingredients for a pizza sauce were thoroughly mixed together and used after standing for at least 1 hour. The sauce was applied to pizza crust followed by baking in an oven at about 230° C. for 12 minutes to prepare pizza.

TABLE 75

| Pizza (8 sheets) | Control | Example |
|---|---|---|
| Hard wheat flour | 250.0 | 250.0 |
| Soft wheat flour | 250.0 | 250.0 |
| Dried yeast | 10.0 | 10.0 |
| Egg (whole) | 80.0 | 80.0 |
| Water | 200.0 | 200.0 |
| Salt | 8.0 | 8.0 |
| Olive oil | 18.0 | 18.0 |
| Sugar | 2.0 | 2.0 |
| Tomato (boiled) | 400.0 | 400.0 |
| Tomato paste | 10.5 | 10.5 |
| Garlic | 15.0 | 15.0 |
| Salt | 5.2 | 5.2 |
| Spices | 2.0 | 2.0 |
| Olive oil | 30.0 | 30.0 |
| Dextrin (Example 6) | — | 60.0 |
| Dietary fiber | 14.1 | 39.0 |
| Dietary fiber/sheet | 1.76 | 4.88 |

Example 52

Food Example 45

An omelet was prepared according to the recipe of Table 76 by dissolving indigestible dextrin in milk, admixing the solution with eggs along with the other ingredients and pan-frying the mixture in salad oil.

TABLE 76

| Omelet | Control | Example |
|---|---|---|
| Egg (whole) | 100.0 | 100.0 |
| Milk | 30.0 | 30.0 |
| Salt | 1.0 | 1.0 |

TABLE 76-continued

| Omelet | Control | Example |
|---|---|---|
| Pepper | 0.2 | 0.2 |
| Salad oil | 5.0 | 5.0 |
| Butter | 5.0 | 5.0 |
| Dextrin (Example 6) | — | 15.0 |
| Dietary fiber | 0.16 | 6.40 |

Example 53

Food Example 46

The materials listed in Table 77 were crushed and mixed together in a raw state to obtain a meat pie ingredient, which was then wrapped with pie dough, followed by baking in an oven at 200° C. for about 30 minutes until the baked mass became colored by scorching to prepare a meat pie.

TABLE 77

| Filling of meat pie | Control | Example |
|---|---|---|
| Poke (minced) | 19.1 | 19.1 |
| Lard | 23.8 | 6.0 |
| Butter | 3.0 | 1.5 |
| Dextrin (Example 6) | — | 12.6 |
| Water | — | 21.4 |
| Milk | 29.6 | 14.8 |
| Milk flavor | — | 0.1 |
| Crumb | 4.1 | 14.1 |
| Egg (whole) | 8.9 | 8.9 |
| Spices | 0.3 | 0.2 |
| Salt | 1.2 | 1.2 |
| Dietary fiber | 0.44 | 5.64 |
| Dietary fiber/50 g | 0.22 | 2.82 |
| Caloric val. 1 (KCal/100 g) | 333 | 205 |
| Caloric val. 2 (KCal/100 g) | 333 | 196 |

Example 54

Food Example 47

A steamed Chinese dumpling stuffed with minced pork and frozen was prepared according to the recipe of Table 78 by mincing the vegetables listed, mixing them with the other materials after removal of water to obtain an inner ingredient, and wrapping the ingredient with a covering, followed by steaming at 100° C. for 5 minutes, then by cooling and thereafter by freezing.

TABLE 78

| Filling of Chinese dumpling | Control | Example |
|---|---|---|
| Poke (minced) | 23.5 | 23.5 |
| Lard | 10.0 | 5.0 |
| Dextrin (Example 7) | — | 2.5 |
| Water | — | 2.5 |
| Chinese cabage | 16.0 | 16.0 |
| Cabage | 22.0 | 22.0 |
| Welsh onion | 7.0 | 7.0 |
| Onion | 14.0 | 14.0 |
| Seasonings and spices | 7.5 | 7.5 |
| Dietary fiber | 0.84 | 1.45 |
| Dietary fiber/80 g | 0.67 | 1.16 |
| Caloric val. 1 (KCal/100 g) | 169 | 137 |
| Caloric val. 2 (KCal/100 g) | 169 | 136 |

Example 55

Food Example 48

According to the recipe of Table 79, ground fish meat, salt and a small amount of ice were mixed together, the mixture was broken and agitated for 5 minutes by a silent cutter, and the other materials and the remaining amount of ice were added to the resulting mixture and mixed therewith for 10 minutes. When the mixture became thickened or viscous at 15° C., the mixture was molded and fried in oil at 160° C. for 4 minutes to obtain fried kamaboko.

TABLE 79

| Kamaboko | Control | Example |
|---|---|---|
| Surimi | 60.0 | 60.0 |
| Salt | 1.8 | 1.8 |
| Ice | 30.4 | 30.4 |
| Starch | 6.0 | 6.0 |
| Seasonings | 1.8 | 1.8 |
| Dextrin (Example 6) | — | 6.0 |
| Dietary fiber | 0.60 | 3.09 |
| Dietary fiber/120 g | 0.72 | 3.50 |

Example 56

Food Example 49

A blackberry liquor was prepared according to the recipe of Table 80 by immersing blackberries in distilled spirits for 40 days, discarding the blackberries and then aging the spirits for 2 months.

TABLE 80

| Black berry liquor | Control | Example |
|---|---|---|
| Black berry | 57.0 | 57.0 |
| Sugar | 34.2 | 17.1 |
| Dextrin (Example 7) | — | 17.0 |
| Aspartame | — | 0.1 |
| White liquor (70 proof) | 65.8 | 65.8 |
| Dietary fiber | 0 | 4.17 |
| Dietary fiber/100 g | 0 | 4.17 |

Example 57

Feed Example 1

Dog food was prepared according to the recipe of Table 81.

TABLE 81

| Dog food | Control | Example |
|---|---|---|
| Corn | 25.0 | 25.0 |
| Wheat and wheat flour | 24.0 | 24.0 |
| Born and meat meal | 16.3 | 16.3 |
| Soy bean waste | 14.4 | 14.4 |
| Fish meal | 4.8 | 4.8 |
| Wheat germ | 2.9 | 2.9 |
| Yeast | 2.9 | 2.9 |
| Animal fat | 3.8 | 3.8 |
| Vitamins and minerals | 5.9 | 5.9 |
| Dextrin (Example 1) | — | 10.0 |
| Dietary fiber | 4.70 | 8.63 |

Example 58

Feed Example 2

Cat food was prepared according to the recipe of Table 82.

TABLE 82

| Cat food | Control | Example |
|---|---|---|
| Corn | 28.4 | 28.4 |
| Wheat flour | 27.3 | 27.3 |
| Brewer's yeast | 3.3 | 3.3 |
| Malt | 3.3 | 3.3 |
| Soy bean waste | 16.4 | 16.4 |
| Fish meal | 0.5 | 0.5 |
| Meat meal | 18.6 | 18.6 |
| Vitamins and minerals | 2.2 | 2.2 |
| Dextrin (Example 1) | — | 10.0 |

TABLE 82-continued

| Cat food | Control | Example |
|---|---|---|
| Dietary fiber | 5.43 | 9.36 |

Example 59

Feed Example 3

A feed for pigs was prepared according to the recipe of Table 83.

TABLE 83

| Pig feed | Control | Example |
|---|---|---|
| Corn | 75.0 | 75.0 |
| Soy bean waste | 11.0 | 11.0 |
| Bran | 3.0 | 3.0 |
| Fish meal | 9.0 | 9.0 |
| Calcium tri-phosphate | 0.7 | 0.7 |
| Calcium carbonate | 0.6 | 0.6 |
| Salt | 0.3 | 0.3 |
| Vitamins | 0.2 | 0.2 |
| Minerals | 0.2 | 0.2 |
| Dextrin (Example 1) | — | 10.0 |
| Dietary fiber | 6.95 | 10.9 |

Example 60

Feed Example 4

A feed for broilers in the initial stage was prepared according to the recipe of Table 84.

TABLE 84

| Feed for broiler | Control | Example |
|---|---|---|
| Corn | 44.65 | 44.65 |
| Milo | 10.0 | 10.0 |
| Soy bean waste | 23.0 | 23.0 |
| Fish meal | 9.0 | 9.0 |
| Gluten meal | 3.0 | 3.0 |
| Alfalfa meal | 2.0 | 2.0 |
| Corn distiller's dried solubles | 1.0 | 1.0 |
| Animal fat | 5.1 | 5.1 |
| Salt | 0.25 | 0.25 |
| Calcium carbonate | 0.6 | 0.6 |
| Calcium di-phosphate | 0.8 | 0.8 |
| Lysine | 0.05 | 0.05 |
| Methionine | 0.18 | 0.18 |
| Vitamins | 0.1 | 0.1 |
| Choline chloride | 0.05 | 0.05 |
| Minerals | 0.1 | 0.1 |
| Nicarbazin | 0.05 | 0.05 |
| Oxytetracycline | 0.07 | 0.07 |
| Dextrin (Example 1) | — | 10.0 |
| Dietary fiber | 7.54 | 11.5 |

Example 61

Feed Example 5

A feed for laboratory rats was prepared according to the recipe of Table 85.

TABLE 85

| Feed for laboratory rat | Control | Example |
|---|---|---|
| Wheat | 12.4 | 12.4 |
| Oat | 18.6 | 18.6 |
| Corn | 10.3 | 10.3 |
| Barley | 34.1 | 34.1 |
| Bran | 3.1 | 3.1 |
| Fish meal | 6.3 | 6.3 |
| Skimmed milk powder | 1.0 | 1.0 |
| Alfalfa | 1.6 | 1.6 |
| Molass | 1.0 | 1.0 |
| Vitamins and minerals | 0.5 | 0.5 |
| Others | 11.1 | 11.1 |

TABLE 85-continued

| Feed for laboratory rat | Control | Example |
|---|---|---|
| Dextrin (Example 1) | — | 10.0 |
| Dietary fiber | 6.22 | 10.2 |

What we claim is:

1. An indigestible dextrin characterized in that the dextrin contains:
   (A) up to 50% of 1→4 glycosidic linkages, and
   (B) at least 60% of an indigestible component,
   (C) the content of indigestible component as actually determined varying within the range of ±5% from a value Y calculated from at least one of equations, i.e., Equations 1 to 62, given below,
   (D) the indigestible dextrin being prepared by adding hydrochloric acid to corn starch and forming a mixture thereof having a Water content of about 5.5% to 8% by weight, and heating the corn starch mixture at 140° to 200° C. using an extruder to react the corn starch in a molten state,
   the value Y being a calculated content (%) of the indigestible component,
   in the equations given below, X1, X2, X3, X4, X5 and X6 have the following meaning and are values quantitatively determined for the dextrin by "Hakomori's methylation method",
   X1: amount (%) of glucose residues at non-reducing ends
   X2: amount (%) of glucose residues having a 1→4 glycosidic linkage
   X3: amount (%) of glucose residues having a 1→6 glycosidic linkage
   X4: amount (%) of glucose residues having a 1→3 glycosidic linkage
   X5: amount (%) of glucose residues having both 1→2 and 1→4 glycosidic linkages
   X6: amount (%) of glucose residues having glycosidic linkages other than the above residues, glucose residues having both 1→4 and 1→6 glycosidic linkages and glucose residues having both 1→3 and 1→4 glycosidic linkages $Y = -64.8 + 4.618 \cdot X1$     1

$Y = 104.8 - 0.934 \cdot X2$     2

$Y = 32.7 + 3.425 \cdot X3$     3

$Y = 47.2 + 3.337 \cdot X4$     4

$Y = -11.7 + 36.852 \cdot X5$     5

$Y = 55 + 3.124 \cdot X6$     6

$Y = 92.1 + 0.349 \cdot X1 - 0.868 \cdot X2$     7

$Y = 29.9 + 0.13 \cdot X1 + 3.335 \cdot X3$     8

$Y = 4.2 + 1.745 \cdot X1 + 2.157 \cdot X4$     9

$Y = -30 + 1.381 \cdot X1 + 26.857 \cdot X5$     10

$Y = -23.5 + 2.974 \cdot X1 + 1.332 \cdot X6$     11

$Y = 59.5 - 0.349 \cdot X2 + 2.159 \cdot X3$     12

$Y = 154.6 - 1.733 \cdot X2 - 2.924 \cdot X4$     13

$Y = 57.6 - 0.559 \cdot X2 + 14.955 \cdot X5$     14

$Y = 115.7 - 1.13 \cdot X2 - 0.731 \cdot X6$     15

$Y = 34.7 + 2.9 \cdot X3 + 0.536 \cdot X4$     16

$Y = 16.4 + 2.206 \cdot X3 + 13.336 \cdot X5$     17

$Y = 34.7 + 3.069 \cdot X3 + 0.377 \cdot X6$     18

$Y = -5.1 + 0.393 \cdot X4 + 32.664 \cdot X5$     19

$Y = 44.3 + 4.805 \cdot X4 - 1.474 \cdot X6$     20

$Y = -27.3 + 45.744 \cdot X5 - 0.835 \cdot X6$     21

$Y = 60.9 - 0.052 \cdot X1 - 0.353 \cdot X2 + 2.18 \cdot X3$     22

$Y = 164.8 - 0.223 \cdot X1 - 1.809 \cdot X2 - 3.045 \cdot X4$     23

$Y = -66 + 1.76 \cdot X1 + 0.249 \cdot X2 + 33.886 \cdot X5$     24

$Y = 180.5 - 1.479 \cdot X1 - 1.61 \cdot X2 - 1.476 \cdot X6$     25

$Y = 34.3 + 0.02 \cdot X1 + 2.889 \cdot X3 + 0.534 \cdot X4$     26

$Y = -5.7 + 0.77 \cdot X1 + 1.276 \cdot X3 + 17.679 \cdot X5$     27

$Y = 27.3 + 0.35 \cdot X1 + 2.789 \cdot X3 + 0.417 \cdot X6$     28

$Y = -42.6 + 1.597 \cdot X1 - 0.584 \cdot X4 + 31.521 \cdot X5$     29

$Y = -22.1 + 2.909 \cdot X1 + 0.111 \cdot X4 + 1.265 \cdot X6$     30

$Y = -36.4 + 1.201 \cdot X1 + 33.184 \cdot X5 - 0.472 \cdot X6$     31

$Y = 184.7 - 2.166 \cdot X2 - 0.776 \cdot X3 - 3.735 \cdot X4$     32

$Y = 30 - 0.135 \cdot X2 + 1.963 \cdot X3 + 10.639 \cdot X5$     33

$Y = 56.2 - 0.302 \cdot X2 + 2.273 \cdot X3 + 0.061 \cdot X6$     34

$Y = 135.3 - 1.552 \cdot X2 - 2.719 \cdot X4 + 5.007 \cdot X5$     35

$Y = 160.5 - 1.819 \cdot X2 - 3.521 \cdot X4 + 0.291 \cdot X6$     36

$Y = 49.9 - 0.644 \cdot X2 + 22.064 \cdot X5 - 0.983 \cdot X6$     37

$Y = 17.9 + 2.185 \cdot X3 + 0.104 \cdot X4 + 12.452 \cdot X5$     38

$Y = 34.5 + 3.189 \cdot X3 - 0.245 \cdot X4 + 0.504 \cdot X6$     39

$Y = 13 + 2.09 \cdot X3 + 15.681 \cdot X5 - 0.104 \cdot X6$     40

$Y = -10.8 + 1.93 \cdot X4 + 34.174 \cdot X5 - 1.681 \cdot X6$     41

$Y = 196.8 - 0.234 \cdot X1 - 2.264 \cdot X2 - 0.811 \cdot X3 - 3.899 \cdot X4$     42

$Y = -39.6 + 1.132 \cdot X1 + 0.233 \cdot X2 + 1.258 \cdot X3 + 24.371 \cdot X5$     43

$Y = 797.3 - 8.856 \cdot X1 - 8.09 \cdot X2 - 11.209 \cdot X3 - 9.1 \cdot X6$     44

$Y = -17.5 + 1.005 \cdot X1 + 1.066 \cdot X3 - 0.363 \cdot X4 + 22.089 \cdot X5$     45

$Y = -17.7 + 2.298 \cdot X1 + 3.1 \cdot X3 - 3.813 \cdot X4 + 2.613 \cdot X6$     46

$Y = -17.5 + 0.869 \cdot X1 + 0.851 \cdot X3 + 24.42 \cdot X5 - 0.275 \cdot X6$     47

$Y = -17.3 + 0.323 \cdot X1 + 1.451 \cdot X4 + 33.667 \cdot X5 - 1.373 \cdot X6$     48

$Y = 105.1 + 0.293 \cdot X1 - 1.294 \cdot X2 - 2.381 \cdot X4 + 9.397 \cdot X5$     49

$Y = 152.4 + 0.284 \cdot X1 - 1.795 \cdot X2 - 3.87 \cdot X4 + 0.535 \cdot X6$     50

$Y = 28.9 + 0.314 \cdot X1 - 0.489 \cdot X2 + 24.497 \cdot X5 - 0.852 \cdot X6$     51

$$Y = 156.6 - 1.84 \cdot X2 - 0.46 \cdot X3 - 3.236 \cdot X4 + 4.127 \cdot X5 \quad (52)$$

$$Y = 177 - 2.056 \cdot X2 - 0.452 \cdot X3 - 3.89 \cdot X4 + 0.24 \cdot X6 \quad (53)$$

$$Y = 55.2 - 0.768 \cdot X2 - 0.491 \cdot X3 + 24.591 \cdot X5 - 1.183 \cdot X6 \quad (54)$$

$$Y = -32.7 + 0.232 \cdot X2 + 2.626 \cdot X4 + 38.544 \cdot X5 - 1.933 \cdot X6 \quad (55)$$

$$Y = -17.5 - 0.522 \cdot X3 + 2.323 \cdot X4 + 39.32 \cdot X5 - 2.035 \cdot X6 \quad (56)$$

$$Y = 16 + 0.81 \cdot X1 - 0.354 \cdot X2 + 0.773 \cdot X3 - 0.916 \cdot X4 + 18.622 \cdot X5 \quad (57)$$

$$Y = -17.7 + 2.506 \cdot X1 + 3.427 \cdot X3 - 4.368 \cdot X4 - 3.553 \cdot X5 + 3.034 \cdot X6 \quad (58)$$

$$Y = 65.4 + 0.304 \cdot X1 - 0.874 \cdot X2 - 1.142 \cdot X4 + 17.26 \cdot X5 - 0.443 \cdot X6 \quad (59)$$

$$Y = -47 + 1.221 \cdot X1 + 0.311 \cdot X2 + 1.394 \cdot X3 + 24.356 \cdot X5 + 0.092 \cdot X6 \quad (60)$$

$$Y = 11.3 + 1.955 \cdot X1 - 0.306 \cdot X2 + 2.571 \cdot X3 - 3.822 \cdot X4 + 2.259 \cdot X6 \quad (61)$$

$$Y = 73.4 - 0.959 \cdot X2 - 0.485 \cdot X3 - 0.58 \cdot X4 + 20.917 \cdot X5 - 0.97 \cdot X6. \quad (62)$$

2. An indigestible dextrin as defined in claim 1 wherein the variation range from the value Y is within ±2%.

3. An indigestible dextrin as defined in claim 1 wherein the content of indigestible component as actually determined varies within the range of ±15% from the value Y calculated from the following equation, i.e., Equation 63:

$$Y = 23.1 + 2.11 \cdot X1 - 0.43 \cdot X2 + 2.819 \cdot X3 - 4.611 \cdot X4 - 5.023 \cdot X5 + 2.71 \cdot X6. \quad (63)$$

4. An indigestible dextrin as defined in claim 3 wherein the variation range from the value Y is within ±10%.

5. An indigestible dextrin as defined in claim 1 which contains:
(A) up to 40% of 1→4 glycosidic linkages, and
(B) at least 70% of the indigestible component.

6. An indigestible dextrin as defined in claim 1 wherein the heating temperature is 140° to 180° C.

7. An indigestible dextrin as defined in claim 1 wherein the extruder is a twin-screw extruder.

8. An indigestible dextrin as defined in any one of claims 1 to 4 which is up to 2.6 kcal/g in caloric value 1.

9. An indigestible dextrin as defined in claim 1 to which is up to 2.2 kcal/g in caloric value 2.

10. An indigestible dextrin as defined in claim 5 which is up to 2.3 kcal/g in caloric value 1.

11. An indigestible dextrin as defined in claim 5 which is up to 1.9 kcal/g in caloric value 2.

12. An indigestible dextrin as defined in claim 1 to which contains a dietary fiber.

13. An indigestible dextrin as defined in claim 1 to which contains at least 2% of a dietary fiber.

14. An indigestible dextrin as defined in claim 5 which contains at least 18% of a dietary fiber.

15. A food containing an indigestible dextrin as defined in claim 1.

16. A food as defined in claim 15 which is a candy, cake, bakery product, ice, snack, beverage or yoghurt.

17. A food as defined in claim 15 which is a soup, mayonnaise, dressing, processed livestock meat product or processed fishery product.

18. An indigestible dextrin as defined in claim 1, wherein the corn starch is heated in the extruder for about 7 to 14.5 seconds.

19. An indigestible dextrin as defined in claim 1, wherein the final product has a water content of from about 1.8% to 1.7%.

* * * * *